(12) United States Patent
Wilsey

(10) Patent No.: US 7,276,147 B2
(45) Date of Patent: *Oct. 2, 2007

(54) METHOD FOR DETERMINING THE CONCENTRATION OF AN ANALYTE IN A LIQUID SAMPLE USING SMALL VOLUME SAMPLES AND FAST TEST TIMES

(75) Inventor: Christopher D. Wilsey, Carmel, IN (US)

(73) Assignees: Roche Diagnostics Operations, Inc., Indianapolis, IN (US); Corange International Limited, Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 10/382,322

(22) Filed: Mar. 5, 2003

(65) Prior Publication Data

US 2004/0031682 A1    Feb. 19, 2004

Related U.S. Application Data

(63) Continuation of application No. 10/264,785, filed on Oct. 4, 2002.

(60) Provisional application No. 60/332,411, filed on Nov. 16, 2001.

(51) Int. Cl.
*G01N 27/327* (2006.01)

(52) U.S. Cl. ............... 205/792; 205/777.5; 204/403.04

(58) Field of Classification Search .................
204/403.01–403.15, 416–418; 205/777.5, 205/778, 792
See application file for complete search history.

(56) References Cited

U.S. PATENT DOCUMENTS

| | | | |
|---|---|---|---|
| 4,759,828 A | 7/1988 | Young et al. | |
| 4,832,814 A | 5/1989 | Root | |
| 5,049,487 A | 9/1991 | Phillips et al. | |
| 5,120,420 A | 6/1992 | Nankai et al. | |
| 5,192,415 A | 3/1993 | Yoshioka et al. | |
| 5,250,439 A | 10/1993 | Musho et al. | |
| 5,262,305 A | 11/1993 | Heller et al. | |
| 5,264,103 A | 11/1993 | Yoshioka et al. | |
| 5,282,950 A | 2/1994 | Dietze et al. | |

(Continued)

FOREIGN PATENT DOCUMENTS

EP    0170375 A2    2/1986

(Continued)

OTHER PUBLICATIONS

Mizutani et al. ("Rapid measurement of transaminase activites using an amperometric L-glutamate-sensing electrode based on a glumate oxidase-poluion complex-bilayer membrane," Sensors and Actuators B 52 (1998) 23-29).*

Morales et al. ("Hydrogen peroxide amperometric biosensor based on a peroxidase-graphite-epoxy biocomposite," Analytica Chimica Acta 332 (1996) 131-138).*

(Continued)

*Primary Examiner*—Alex Noguerola
(74) *Attorney, Agent, or Firm*—Woodard, Emhardt, Moriarty, McNett & Henry LLP

(57) ABSTRACT

Analytes in a liquid sample are determined by methods utilizing sample volumes of less than about 1.5 μl and test times within ten seconds. The methods are preferably performed using small test strips including a sample receiving chamber filled with the sample by capillary action.

69 Claims, 6 Drawing Sheets

U.S. PATENT DOCUMENTS

| | | | |
|---|---|---|---|
| 5,288,636 A * | 2/1994 | Pollmann et al. | 204/403.14 |
| 5,352,351 A | 10/1994 | White et al. | |
| 5,354,447 A | 10/1994 | Uenoyama et al. | |
| 5,389,215 A | 2/1995 | Horiuchi et al. | |
| 5,437,772 A | 8/1995 | De Castro et al. | |
| 5,437,999 A | 8/1995 | Diebold | |
| 5,508,171 A | 4/1996 | Walling et al. | |
| 5,509,410 A | 4/1996 | Hill et al. | |
| 5,565,085 A * | 10/1996 | Ikeda et al. | 205/777.5 |
| 5,575,895 A | 11/1996 | Ikeda et al. | |
| 5,611,900 A | 3/1997 | Worden et al. | |
| 5,650,062 A * | 7/1997 | Ikeda et al. | 205/778 |
| 5,658,443 A | 8/1997 | Yamamoto et al. | |
| 5,670,031 A | 9/1997 | Hintsche et al. | |
| 5,698,083 A | 12/1997 | Glass | |
| 5,708,247 A | 1/1998 | McAleer et al. | |
| 5,723,345 A | 3/1998 | Yamauchi et al. | |
| 5,762,770 A | 6/1998 | Pritchard et al. | |
| 5,820,551 A | 10/1998 | Hill et al. | |
| 5,858,691 A | 1/1999 | Hoenes et al. | |
| 5,863,400 A | 1/1999 | Drummond et al. | |
| 6,004,441 A | 12/1999 | Fujiwara et al. | |
| 6,042,714 A | 3/2000 | Lin et al. | |
| 6,103,509 A | 8/2000 | Sode | |
| 6,120,676 A | 9/2000 | Heller et al. | |
| 6,143,164 A | 11/2000 | Heller et al. | |
| 6,153,069 A | 11/2000 | Pottgen et al. | |
| RE36,991 E | 12/2000 | Yamamoto et al. | |
| 6,156,173 A | 12/2000 | Gotoh et al. | |
| 6,193,873 B1 | 2/2001 | Ohara et al. | |
| 6,212,417 B1 | 4/2001 | Ikeda et al. | |
| 6,241,862 B1 | 6/2001 | McAleer et al. | |
| 6,258,229 B1 | 7/2001 | Winarta et al. | |
| 6,270,637 B1 | 8/2001 | Crismore et al. | |
| 6,284,125 B1 | 9/2001 | Hodges | |
| 6,338,790 B1 | 1/2002 | Feldman et al. | |
| 6,475,372 B1 | 11/2002 | Ohara et al. | |
| 6,582,573 B2 | 6/2003 | Douglas et al. | |
| 6,592,745 B1 | 7/2003 | Feldman et al. | |
| 6,890,421 B2 | 5/2005 | Ohara et al. | |
| 2002/0092612 A1 | 7/2002 | Davies et al. | |
| 2005/0176153 A1 | 8/2005 | O'hara et al. | |

FOREIGN PATENT DOCUMENTS

| | | |
|---|---|---|
| EP | 0206218 A2 | 12/1986 |
| EP | 0359831 B1 | 3/1990 |
| EP | 0467219 B1 | 1/1992 |
| EP | 0 859 230 | 8/1998 |
| EP | 0 964 059 | 12/1999 |
| EP | 0585113 B1 | 12/1999 |
| EP | 1067384 A2 | 1/2001 |
| EP | 1119637 B1 | 8/2001 |
| EP | 1252514 B1 | 10/2002 |
| EP | 1269173 B1 | 1/2003 |
| JP | 05312761 A1 | 11/1993 |
| JP | 002874 A1 | 1/1998 |
| JP | 1194790 A1 | 4/1999 |
| JP | 1194791 A1 | 4/1999 |
| JP | 11108879 A1 | 4/1999 |
| JP | 11125618 A1 | 5/1999 |
| WO | WO86/07632 | 12/1986 |
| WO | WO95/22597 | 8/1995 |
| WO | WO95/22597 A1 | 8/1995 |
| WO | WO9528634 A1 | 10/1995 |
| WO | WO97/00441 A1 | 1/1997 |
| WO | WO97/18465 A1 | 5/1997 |
| WO | WO97/30344 | 8/1997 |
| WO | WO98/35225 A1 | 8/1998 |
| WO | WO9835225 A1 | 8/1998 |
| WO | WO99/17115 A1 | 4/1999 |
| WO | WO 00/20626 | 4/2000 |
| WO | WO00020626 A1 | 4/2000 |
| WO | WO00/42422 A1 | 7/2000 |
| WO | WO 00/73778 | 12/2000 |
| WO | WO 01/25775 | 4/2001 |
| WO | WO01/57510 A1 | 8/2001 |
| WO | WO01/67099 A1 | 9/2001 |
| WO | WO 01/73124 | 10/2001 |

OTHER PUBLICATIONS

CAPLUS abstract of Mizutani et al. (Amperometric enzyme electrode with fast response to glucose using a layer of lipid-modified glucose oxidase and Nafion anionic polymer, Analytica Chimica Acta (1993), 274(2), 201-7).*

CAPLUS abstract of Mizutani et al. ("Amperometric glucose sensor using a polyion complex-enzyme bilayer system," Chemica Sensors (1997), 13(Suppl. B, Proceedings of the 25th Chemical Sensor Symposium, 1997), 37-40).*

CAPLUS abstract of Rishpon et al. ("Amperometric glucose sensors based on glucose oxidase immobilized in Nafion," Electroanalysis (1994), 6(1), 17-21).*

Lifescan press release for the One Touch Ultra System (downloaded Oct. 9, 2004 from www.lifescan.com/company./about/press/prultra).*

Xin et al. ("Enzyme modified amperometric sensors for choline and acetylene with tetrathiafulvalene tetracyanoquinodimethane as the electron-transfer mediator," Analytica Chimica Acta 341 (1997) 43-51).*

Lei et al. ("Studies on employing tetrathiafulvalene as an electron shuttle incorporated in a montmotillonite-modified immobilization matrix for an enzyme electrode," Journal of Electroanalytical Chemistry 419 (1996) 93-98).*

Chen et al. ("β-Cyclodextrin cation exchange polymer membrane for improved second-generation glucose biosensor," Analytica Chimica Acta 306 (1995) 201-208).*

Losada et al. ("Glucose Ampermetric Sensor Based on Covalent Immobilization Glucose Oxidase in Poly-2-aminoanailine Film via Chloranil on Platinized Platinum Electrode," Elecrtoanalysis 1997, 9, No. 18).*

Aoki, K.; Morita, M.; Niwa, O.; and Tabei, H. "Quantitative Analysis Of Reversible Diffusion Controlled Currents Of Redox Soluble Species At Interdigitated Array Electrodes Under Steady-State Conditions", J. Electroanal. Chem. 256 (1988) 269-282.

Aoki, K. and Tanaka, M.; "Time-Dependence Of Diffusion-Controlled Currents Of A Soluble Redox Couple At Interdigitated Microarray Electrodes" J. Electroanal. Chem. 266 (1989) 11-20.

Niwa, O.; Morita, M.; and Tabei H., "Electrochemical Behavior Of Reversible Redox Species At Interdigitated Array Electrodes With Different Geometries: Consideration Of Redox Cycling and Collection Efficiency" Anal. Chem. 62 (1990) 447-452.

Nishihara H., Dalton F., and Murray R.W., "Interdigitated array Electrode Diffusion Measurements in Donor/Acceptor Solutions in Polyether Electrolyte Solvents", Anal. Chem. 1991, 63, 2955-2960.

Hintsche, R. et al., "Chip Biosensors On Thin-Film Metal Electrodes", Sensors and Actuators B. 4 (1991) 287-291.

Wollenberger, U; Paischke, M.; and Hintche, R. "Interdigitated Array Microelectrodes For The Determination Of Enzyme Activities", Analyst, Jun. 1994, 1245-1249.

Paeschke, M; Wollenberger, U.; Kohler, C.; et al., "Properties Of Interdigital Electrode Arrays With Different Geometries" Analytica Chimica Acta 305 (1995) 126-136.

Jin, B.; Qian, W.; Zhang, Z.; and Shi, H. "Application Of The Finite Analytic Numerical Method. Part I. Diffusion Problems On Coplanar and Elevated Interdigitated Microarray Band Electrodes" J. Electroanal. Chem. 441 (1996) 29-36.

Miao et al, "Amperometric Glucose Biosensor Based on Immobilization of Glucose Oxidase in Chitosan Matrix Cross-Linked with Glutaraldehyde", Electroanalysis, 2001, vol./Issue No. 13, No. 4, pp. 347-349.

Chiba, K.; Ohsaka, T.; Ohnuki, Y.; and Oyama, N., *"Electrochemical Preparation of a Ladder Polymer Containing Phenazine Rings"*, J. Electroanal. Chem., 219 (1987) 117-124.

Bartlett, P.N. and Whitaker, R.G., "*Electrochemical Immobilisation of Enzymes: Part I. Theory*", J. Electroanal. Chem., 224 (1987) 27-35.
Bartlett, P.N. and Whitaker, R.G., "*Electrochemical Immobilisation of Enzymes: Part II. Glucose Oxidase Immobilised in Poly-N-Methylpyrrole*", J. Electroanal. Chem., 224 (1987) 37-48.
Malitesta, Cosimino; Palmissano, Francesco *; Torsi, Luisa; and Zambonin Pier Giorgio, "Glucose Fast-Response Amperometric Sensor Based on Glucose Oxidase Immobilized in an Electropolymerized Poly(o-phenylenediamine) Film", *Anal. Chem. 1990*, 62, 2735-2740.
Gregg, Brian A. and Heller, Adam, "*Cross-Linked Redox Gels Containing Glucose Oxidase for Amperometric Biosensor Applications*", Anal. Chem. 1990, 62, 258-263.
Lee, Jae-Suk; Nakahama, Seiichi; and Hirao, Akira, "A New Glucose Sensor Using Microporous Enzyme Membrane", *Sensors and Actuators B*, 3 (1991) 215-219.
Burke, David W. and Surridge, Nigel A., "Improved-Accuracy Biosensor Strip for Accu-Chek™ Advantage® ", presented orally at ACS Boston Meeting (~1993-1994).
Miao, Y.; Chia, L.S.; Goh, N.K.; and Tan, S.N., "Amperometric Glucose Biosensor Based on Immobilization of Glucose Oxidase in Chitosan Matrix Cross-Linked with Glutaraldehyde", *Electroanalysis 2001*, 13, No. 4.
Lifescan product brochue for OneTouch® Ultra™ Test Strip, publn. date not available.
Photocopies of the front and back portions of the commercial product marketed by Lifescan as the OneTouch made public at least as early as 2001.
Owner's Booklet entitled "The Comfort of Control" by Lifescan, publn. date not available.
"Quick Start Guide" for the Onetouch® Ultra™ Blood Glucose Monitoring System.
Bartlett et al, "Electrochemical Immobilisation of Enzymes—Part II Glucose Oxidase Immobilised in Poly-N-Methylpyrrole", J. Electroanal. Chem., 1987, vol./Issue No. 224, pp. 37-48.
Bartlett et al, "electrochemical Immobilisation of Enzymes—Part I Theory", J. Electroanal. Chem., 1987, vol./Issue No. 224, pp. 27-35.
Burke et al, "Improved-Accuracy Biosensor Strip for Accu-Chek Advantage", ACS Boston Meeting, Presented Orally 1993-1994, pp. 29-61.
Chiba et al, "Electrochemical Preparation of a Ladder Polymer Containing Phenazine Rings", J. Electroanal. Chem., 1987, vol./Issue No. 219, pp. 117-124.
Gregg et al, "Cross-Linked Redox Gels Containing Glucose Oxidase for Amperometric Biosensor Applications", Anal. Chem., 1990, vol./Issue No. 62, pp. 258-263.
Lee et al, "A New Glucose Sensor Using Microporous Enzyme Membrane", Sensors and Actuators, 1991, vol./Issue No. B,3, pp. 215-219.
LIFESCAN, "Blood Glucose Monitoring Systems—Current Technologies", 1998, Lifescan Technical Support Publications Group.
Lifescan Guide, "Quick Start" Onetouch Ultra Blood Glucose Monitoring System, publn. date not available.
Lifescan Owner's Booklet, "The Comfort of Control" Onetouch Ultra Blood Glucose Monitoring System, publn. date not available.
Lifescan Product Brochure, "Onetouch Ultra Test Strips", Lifescan Inc., 2000.
Lifescan Product Brochure, "Onetouch Ultra Blood Glucose Monitoring System" New!, publn. date not available.
Malitesta et al., "Glucose Fast-Response Amperometric Sensor Based on Glucose Oxidase Immobilized in an Electropolymerized Poly(O-phenylenediamine) Film", Anal. Chem., 1990, vol./Issue No. 62 pp. 2735-2740.
McMahon et al, "Detection Technologies—Taking a fresh look at sensors", IVD Technology, Apr. 2002, www.devicelink.com/ivd/archive/02/04/002.html.
Translation of JP H10 [1998]-02874.
Translation of JP H05[1993]-312761.
Translation of JP H11[1999]-108879.
Translation of JP H11[1999]-125618.
Translation of JP H11[1999]-94790.
Translation of JP H11[1999]-94791.

Opposition Brief Against European Patent 1 269 173 by Roche Diagnostics GmbH, May 16, 2006.
Enclosures A, B, C1, C2, C3, and C4 of Opposition Brief Against European Patent 1 269 173 by Roche Diagnostics GmbH, May 16, 2006 - TheraSense blood glucose monitoring system; prior public use and documentation about this earlier product.
US District Court Northern District of California No. C 05-3177 - Abbott's Complaint, Aug. 1, 2005.
US District Court Northern District of California Case No. C 05-3177 - Roche's Answer, Aug. 22, 2005.
US District Court Northern District of California Case No. C 05-3177 - Abbott's First Amended complaint, Oct. 4, 2005.
US District Court Northern District of California Case No. C 05-3177 - Roche's Answer to First Amended Complaint, Oct. 18, 2005.
US District Court Northern District of California Case No. C 05-3177-Abbott's Reply to Counterclaims, Nov. 8, 2005.
US District Court Northern District of California Case No. C 05-3177-Roche's Preliminary Invalidity Contentions, Dec. 9, 2005.
US District Court Northern District of California Case No. 05-3177-Roche's Second Amended Preliminary Invalidity Contentions, Sep. 15, 2006.
US District Court Northern District of California Case No. C 05-3177-Abbott's Opening Markman Brief, Dec. 1, 2006.
US District Court Northern District of California Case No. C 04-2123, C 04-3327, C 04-3732-Abbott's Opening Markman Brief, Dec. 1, 2006.
US District Court Northern District of California Case No. C 04-2123, C 04-3327, C 04-3732-Becton Dickinson's Opening Markman Brief, Dec. 1, 2006.
US District Court Northern District of California Case No. C 05-3177-Roche and Bayer's Opening Markman Brief, Dec. 1, 2006.
US District Court Northern District Of California Case No. C 04-2123, C 04-3327, C 04-3732-Abbott's Reply Markman Brief, Dec. 20, 2006.
US District Court Northern District of California Case No. C 05-3177-Abbott's Reply Markman Brief, Dec. 20, 2006.
US District Court Northern District of California Case No. C 05-3177-Bayer's Reply Markman Brief, Dec. 20, 2006.
US District Court Northern District of California Case NO. C 04-2123, C 04-3327, C 04-3732-Becton Dickson's Reply Markman Brief, Dec. 20, 2006.
US District Court Northern District of California Case No. C 05-3177-Roche's Reply Markman Brief, Dec. 20, 2006.
US District Court Northern District of California No. C 05-3177-Docket Report, Mar. 22, 2007.
Feldman et al, "FreeStyle TM: A Small-Volume Electrochemical Glucose Sensor for Home Blood Glucose Testing", Diabetes Technology & Therapeutics, vol. 2, No. 2, 2000, Mary Ann Liebert, Inc.
Abbott's Response to Opposition Brief Against European Patent 1 119 637, Oct. 1, 2005.
Agamatrix Opposition Brief Against European Patent 1 119 637, Dec. 22, 2004.
Agamatrix First Supplemental Brief Against European Patent 1 119 637, Jun. 22, 2006.
Letter regarding European Patent Application No. 98906328.4-2204 TheraSense, Inc., Mar. 23, 2001.
N.A. Morris et al., "An Electrochemical Capillary Fill Device for the Analysis of Glucose Incorporating Glucose Oxidase and Ruthenium (III) Hexamine as Mediator", Electroanalysis 4 (1992) 1-9.
Opposition Brief Against European Patent 1 119 637 by Roche Diagnostics GmbH, Dec. 23, 2004.
First Supplemental Opposition Brief Against European Patent 1 119 637 by Roche Diagnostics GmbH, Jun. 9, 2006.
Second Supplemental Opposition Brief Against European Patent 1 119 637 by Roche Diagnostics GmbH, Oct. 13, 2006.
Response to Opposition of EP 1269173 dated May 3, 2007-Diabetes Diagnostics, Inc.
Chiba, K.; Ohsaka, T.; Ohnuki, Y.; and Oyama, N., "*Electrochemical Preparation of a Ladder Polymer Containing Phenazine Rings*", J. Electroanal. Chem., 219 (1987) 117-124.

Bartlett, P.N. and Whitaker, R.G., "*Electrochemical Immobilisation of Enzymes: Part I. Theory*", J. Electroanal. Chem., 224 (1987) 27-35.

Bartlett, P.N. and Whitaker, R.G., "*Electrochemical Immobilisation of Enzymes: Part II. Glucose Oxidase Immobilised in Poly-N-Methylpyrrole*", J. Electroanal. Chem., 224 (1987) 37-48.

Malitesta, Cosimino; Palmissano, Francesco*; Torsi, Luisa; and Zambonin Pier Giorgio, "Glucose Fast-Response Amperometric Sensor Based on Glucose Oxidase Immobilized in an Electropolymerized Poly (o-phenylenediamine) Film", *Anal. Chem.* 1990, 62, 2735-2740.

Gregg, Brian A. and Heller, Adam, "*Cross-Linked Redox Gels Containing Glucose Oxidase for Amperometric Biosensor Applications*", Anal. Chem. 1990, 62, 258-263.

Lee, Jae-Suk; Nakahama, Seiichi; and Hirao, Akira, "A New Glucose Sensor Using Microporous Enzyme Membrane", *Sensors and Actuators B*, 3 (1991) 215-219.

Burke, David W. and Surridge, Nigel A, "Improved Accuracy Biosensor Strip for Accu-Chek™ Advantage®", presented orally at ACS Boston Meeting (~1993-1994).

Miao, Y.; Chia, L.S.; Goh, N.K.; and Tan, S.N., "Amperometric Glucose Biosensor Based on Immobilization of Glucose Oxidase in Chitosan Matrix Cross-Linked with Glutaraldehyde", *Electroanalysis* 2001, 13, No. 4.

Lifescan product brochure for OneTouch® Ultra™ Test Strip.

Photocopies of the front and back portions of the commercial product marketed by Lifescan as the OneTouch made public at least as early as 2001.

Owner's Booklet entitled "The Confort of Control" by Lifescan, date unavailable.

"Quick Start Guide" for the OneTouch® Ultra™ Blood Glucose Monitoring System, date unavailable.

* cited by examiner

METHOD FOR DETERMINING THE CONCENTRATION OF AN ANALYTE IN A LIQUID SAMPLE USING SMALL VOLUME SAMPLES AND FAST TEST TIMES

REFERENCE TO RELATED APPLICATIONS

This application is a continuation-in-part of U.S. patent application Ser. No. 10/264,785, filed on Oct. 4, 2002, which claims the benefit of U.S. Provisional Patent Application No. 60/332,411, filed on Nov. 16, 2001.

FIELD OF THE INVENTION

The present invention relates to methods for determining the concentration of an analyte in a liquid sample, and particularly to methods using sample volumes of less than 1.5 µl and test times within ten seconds after application of the sample.

BACKGROUND

Electrodes are well known devices which permeate industry, and which, although often very small in size and not particularly visible, can have a significant impact on peoples' lives. Electrodes are used in electronic instruments having many industrial, medical, and analytical applications. To name just a few, they include monitoring and controlling fluid flow, and various types of analytical methods wherein electric current is measured to indicate the presence or concentration of certain chemical species.

With respect to analytical methods, the need for detection and quantitative analysis of certain chemicals found within a larger composition can be important for the chemical and manufacturing industries, as well as biotechnology, environmental protection, and health care industries. Examples of substances that may be analyzed include liquid samples such as tap water, environmental water, and bodily fluids such as blood, plasma, urine, saliva, interstitial fluid, etc.

Many analytical techniques, sometimes referred to as electrochemical detection methods, make use of electrodes as a component of an electrochemical sensor. The sensors are used in combination with electronic apparatuses to precisely detect the presence or concentration of a selected chemical species (analyte) within a substance sample. Techniques that allow the use of miniaturized disposable electroanalytic sample cells for precise micro-aliquote sampling, and self-contained, automatic means for measuring the analysis, can be particularly useful.

Electrochemical detection methods can include amperometric measurement techniques, which generally involve measurement of a current flowing between electrodes that directly or indirectly contact a sample of a material containing an analyte, and studying the properties of the current. The magnitude of the current can be compared to the current produced by the system with known samples of known composition, e.g., a known concentration of analyte, and the quantity of analyte within the sample substance can be deduced. These types of electrochemical detection methods are commonly used because of their relatively high sensitivity and simplicity.

Micro-electrode arrays are structures generally having two electrodes of very small dimensions, typically with each electrode having a common element and electrode elements or micro-electrodes. If "interdigitated" the arrays are arranged in an alternating, finger-like fashion (See, e.g., U.S. Pat. No. 5,670,031). These are a sub-class of micro-electrodes in general. Interdigitated arrays of micro-electrodes, or IDAs, can exhibit desired performance characteristics; for example, due to their small dimensions, IDAs can exhibit excellent signal to noise ratios.

Interdigitated arrays have been disposed on non-flexible substrates such as silicon or glass substrates, using integrated circuit photolithography methods. IDAs have been used on non-flexible substrates because IDAs have been considered to offer superior performance properties when used at very small dimensions, e.g., with feature dimensions in the 1–3 micrometer range. At such small dimensions, the surface structure of a substrate (e.g., the flatness or roughness) becomes significant in the performance of the IDA. Because non-flexible substrates, especially silicon, can be processed to an exceptionally smooth, flat, surface, these have been used with IDAs.

SUMMARY OF THE INVENTION

Whereas micro-electrodes have in the past been used with non-flexible substrates such as silicon, ceramic, glass, aluminum oxide, polyimide, etc., it has now been discovered that micro-electrode arrays, for example, IDAs, can be advantageously useful when disposed on flexible substrates. Moreover, such micro-electrodes, disposed on flexible surfaces, can be prepared using methods that involve flexible circuit photolithography, as opposed to methods relating to integrated circuit photolithography.

An interdigitated array of the invention, disposed on a flexible substrate, can be used generally, in applications where IDAs are known to be usefully employed. In particular embodiments of the invention, the IDAs can be used to construct electrochemical sensors, test cells, or test strips. The sensors can be used with electronic detection systems (sometimes referred to as "test stands") in methods of analyzing sample compositions for analytes. Preferred embodiments of sensors can be disposable, and can include channels or microchannels, preferably a capillary, which facilitates flow of a substance sample into the reaction chamber and in contact with the sensor.

The micro-electrode arrays of the invention can be useful when disposed onto a flexible substrate. In particular, IDAs are shown to be effective at dimensions relatively larger than the dimensions often used for IDAs disposed on non-flexible substrates. Even though they can be relatively larger than IDAs disposed on non-flexible substrates, the inventive IDAs are still able to exhibit performance properties, e.g., signal to noise amplification benefits and steady-state assay profiles, comparable to IDAs having smaller dimensions.

Electrochemical sensors of the invention have been found to provide performance advantages, e.g., relative to commercially available sensors. For sensors used in glucose monitoring, compared to commercially available sensors, the inventive sensors can exhibit improved (shortened) processing periods, e.g., one half second to steady-state after application of the assay potential and 5 seconds to readout, and the ability to get an accurate and precise readout from a relatively small sample of substance, e.g., less than one microliter (µl), preferably a sample volume in the range from about 0.25 to 1.0 µl e.g., from about 0.4 to about 1.0 µl.

The use of larger-dimensioned micro-electrode arrays also allows the significant advantage of fabricating arrays and sensors using relatively less expensive and more efficient flex circuit photolithography processes. These can advantageously incorporate the use of solid materials instead of spin-on liquid materials, e.g., one or more of a solid photoresist or a solid coverlay, instead of liquid materials typically used in integrated circuit photolithography.

An aspect of the invention relates to micro-electrodes used in combination with a flexible substrate. The array can include a working electrode and a counter electrode, each including a common lead and commonly-connected electrode elements, for example with the electrode elements being arranged in a substantially-parallel, alternating fashion. Preferred dimensions for micro-electrodes can be, e.g., feature size or width of electrodes ($W_e$) in the range from 15 or 20 or 25 µm, up to about 100 µm, more preferably from greater than or about 25 or 30 µm to about 50 µm. Preferred spacing between electrodes ($W_g$) can also be in the range from about 15 to about 50 µm, more preferably from greater than or about 20 or 25 µm to about 45 µm.

Another aspect of the invention relates to an electrochemical sensor comprising an array of micro-electrodes disposed on a flexible substrate. The sensor can further include a chemical coating disposed on the array to facilitate practice of electrochemical detection methods.

Yet another aspect of the invention relates to a method of detecting an analyte using an array of micro-electrodes of the invention, e.g., using an electrochemical sensor comprising an interdigitated array disposed proximal to a flexible substrate. Such a method can include certain of the following steps. A sensor is provided which comprises micro-electrodes proximal to a flexible substrate, and a chemical coating proximal to the micro-electrodes; the coating comprises a compound reactive to produce an electroactive reaction product. The coating is contacted with a substance comprising an analyte, allowing the analyte to react with chemical components of the coating to produce an electroactive reaction product. Electric properties of the coating can be measured, and the electric properties can be correlated to the amount of electroactive reaction product, and to the amount of analyte.

Still another aspect of the invention relates to a method of preparing a micro-electrode, including the step of disposing the micro-electrode onto a flexible substrate.

More particularly, the present invention comprises a method for determining the concentration of glucose in a blood sample. The method utilizes a disposable test strip having a capillary-fill chamber including a working electrode and a counter and/or reference electrode and a reagent. The reagent includes an enzyme and a mediator, and reacts with glucose to produce an electroactive reaction product. The method involves providing a blood sample to the capillary chamber and detecting the presence of the blood sample in the capillary chamber. Within 10 seconds of detecting the presence of the blood sample, the glucose concentration is determined.

DETAILED DESCRIPTION

Figure 1:
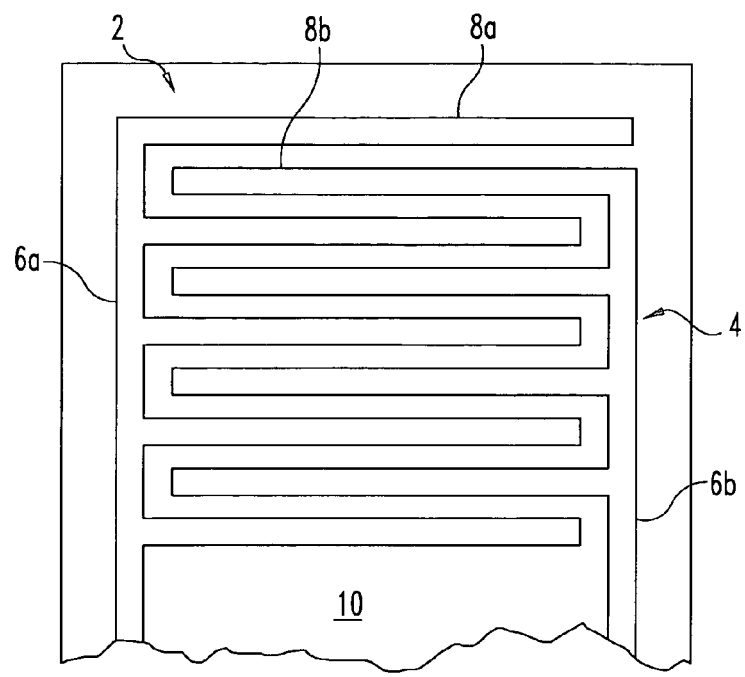
FIG. 1 shows an embodiment of an interdigitated array of the invention.

An embodiment of the present invention is directed to arrays of micro-electrodes, e.g., an interdigitated array of electrodes (sometimes referred to as "microband" electrodes) used in combination with a flexible substrate.

An array of micro-electrodes includes two electrodes, referred to as the working electrode and the counter electrode, electrically insulated from one another.

Micro-electrodes, as distinguished from other electrodes generally, are understood in the electronic and biosensor arts. In analyzing a liquid sample using electrodes and electronic equipment and techniques, the size and spacing of electrodes can affect whether diffusion of an analyte through the sample to an electrode occurs by a planar or non-planar path. Micro-electrode arrays are of a size and spacing such that in detecting chemical species of a solution, the species will diffuse toward or approach an electrode of the micro-electrode array in a non-planar fashion, e.g., in a curved or hemispherical path of diffusion. In contrast, non-microelectrodes, i.e., "macro-electrodes," cause diffusion of an analyte through a solute according to a substantially planar path. It is also understood that some electrode configurations can cause diffusion to take place by a mix of planar and non-planar paths, in which case the electrodes can be considered a micro-electrode array, especially if the diffusion occurs predominantly (e.g., greater than 50%) according to a non-planar path, or if the size of the electrodes is less than 100 µm, e.g., less than 50 µm.

The electrodes of a micro-electrode array are positioned near each other in an arrangement that will result in non-planar diffusion as described. The arrangement of the electrodes can be any arrangement that results in such diffusion, with a working and a counter electrode being substantially evenly spaced from each other. One electrode may be arranged into a shape or figure or outline that will produce interstices within which the second electrode may be placed. For instance, one electrode can be arranged as an increasing radius, substantially circular spiral, with a continuous, long and narrow interstitial area being created between each successively larger revolution of electrode. The other electrode can be positioned in the interstitial area between revolutions, while the electrodes remain insulated from one another. The width and spacing of the electrodes can be arranged to result in micro-electrode array performance.

According to other forms of such micro-electrode arrays, the spiral may not be substantially circular, but could include linear, square, angled, or oblong or oval features. Or, the electrodes could be arranged in any other geometric form whereby the electrodes are placed adjacent to each other and within the other's respective interstitial area, e.g., by following a similar path separated by a substantially uniform gap.

In one particular embodiment, the micro-electrode can be arranged into an interdigitated array, meaning that at least a portion of electrode elements of the working electrode are placed substantially parallel to and in alternating succession with at least a portion of the electrode elements of the counter electrode, e.g., in an alternating, "finger-like" pattern. Such interdigitated micro-electrode arrays include electrode elements (sometimes referred to as "fingers") and a common element ("contact strip") which commonly connects the electrode elements.

The components of the electrodes may be made of any conductive material, including those known and conventionally used as electrode materials, particularly including materials known in the flexible circuit and photolithography arts.

These can include, for example, carbon, noble metals such as: gold, platinum, palladium, alloys of these metals, potential-forming (conductive) metal oxides and metal salts, as well as others.

The electrodes and their components can be of dimensions, meaning the width of the electrode components as well as the separation between components, that can provide an array with useful properties, e.g., useful or advantageous capabilities with respect to contacting a substance or measuring electrical properties. Advantageously, interdigitated arrays can be prepared at dimensions that allow for contact with and measurement of electrical properties of a relatively small sample of a substance.

In preferred embodiments of the invention, each electrode element can independently have a width ($W_e$) in the range from greater than 15 micrometers (μm) to about 50 μm, with the range from greater than or about 20 or 25 μm to about 40 μm being particularly preferred. The separation between electrode components ($W_g$), especially the separation between alternating electrode elements, can also preferably be in the range between about 15 micrometers and about 50 μm, with the range from greater than or about 20 or 25 μm to about 40 μm being particularly preferred. The total area of an electrode (meaning the area of the fingers but not the common element) can be chosen depending on these dimensions, on the use intended for the electrode, on the desired current level intended to pass through the electrode, and on the desired number of electrode elements. An exemplary area of an electrode having 10 electrode elements can be in the range from about 0.1 to about 0.5 square millimeters, (for example 10 electrode fingers having dimensions of 50 μm by 1 mm), e.g., from about 0.2 to 0.3.

The thickness of the electrode components can be sufficient to support a desired electric current. Exemplary thicknesses can be in the range from about 30 to 200 nanometers (nm), with a preferred thickness being about 100 nm.

The electrodes can independently have a number of interdigitated electrode elements sufficient to provide utility, e.g., allowing contact with a substance to measure its electrical behavior. Conventionally, the array can have substantially the same number (equal, plus or minus one) of electrode elements in the working electrode as are in the counter electrode, allowing the electrode elements to be paired next to each other in an alternating sequence. In some preferred embodiments of the array, such as in some of the applications described below for electrochemical sensors, each electrode of an array may typically have from about 4 to about 30 electrode elements.

FIG. 1 illustrates an embodiment of an array of the invention. Working electrode 2 and counter electrode 4 are arranged as an interdigitated array on flexible substrate 10. (The figure is not to scale and its dimensions, as well as the dimensions of the other figures, should not be construed to limit the invention). The working and counter electrodes include common strips 6a and 6b, respectively, which can be connected to electrically conductive means (e.g., "connectors," "pads," or "leads," etc.) for connecting the electrodes to an external circuit. In the illustrated example, the working electrode includes electrode elements 8a connected to common strip 6a, and the counter electrode includes electrode elements 8b connected to common strip 6b.

According to the invention, the interdigitated array is disposed proximal to, e.g., on, a flexible substrate. To act as a flexible substrate, a material must be flexible and also insulating, and is typically relatively thin. The substrate should be capable of adhering components of an IDA, or additional components of a sensor, to its surface. Such thin, insulative, flexible substrates are known in the art of flexible circuits and flex circuit photolithography. "Flexible substrates" according to the present disclosure can be contrasted to non-flexible substrates used in integrated circuit (IC) photolithography but not in flexible circuit photolithography. Examples of non-flexible substrates used in IC photolithography include silicon, aluminum oxide, and other ceramics. These non-flexible substrates are chosen to be processable to a very flat surface. Typical flexible substrates for use in the invention are constructed of thin plastic materials, e.g., polyester, especially high temperature polyester materials; polyethylene naphthalate (PEN); and polyimide, or mixtures of two or more of these. Polyimides are available commercially, for example under the trade name Kapton®, from I.E. duPont de Nemours and Company of Wilmington, Del. (duPont). Polyethylene naphthalate is commercially available as Kaladex®, also from duPont. A particularly preferred flexible substrate is 7 mil thick Kaladex® film.

Interdigitated arrays of the invention can be used in applications generally known to incorporate electrodes, especially applications known to involve interdigitated arrays of electrodes. Various applications are known in the arts of electronics and electrochemistry, including applications relating to process and flow monitoring or control, and chemical analytical methods. The arrays may be particularly useful as a component of an electrochemical sensor, where there is added value, benefit, or cost efficiency, to the use of a flexible substrate, or where there is value, benefit, or cost efficiency in having an interdigitated array of dimensions relatively larger than the dimensions of interdigitated arrays conventionally disposed on non-flexible substrates.

An interdigitated array of the invention can, for example, be included in an electrochemical sensor (sometimes referred to as a "biosensor" or simply "sensor") used in electrochemical detection methods. Electrochemical detection methods operate on principles of electricity and chemistry, or electrochemistry, e.g., on principles of relating the magnitude of a current flowing through a substance, the resistance of a substance, or a voltage across the substance given a known current, to the presence of a chemical species within the substance. Some of these methods can be referred to as potentiometric, chronoamperometric, or impedence, depending on how they are practiced, e.g., whether potential difference or electric current is controlled or measured. The methods and sensors, including sensors of the invention, can measure current flowing through a substance due directly or indirectly to the presence of a particular chemical compound (e.g., an analyte or an electroactive compound), such as a compound within blood, serum, interstitial fluid, or another bodily fluid, e.g., to identify levels of glucose, blood urea, nitrogen, cholesterol, lactate, and the like. Adaptations of some electrochemical methods and electrochemical sensors, and features of their construction, electronics, and electrochemical operations, are described, for example, in U.S. Pat. Nos. 5,698,083, 5,670,031, 5,128,015, and 4,999,582, each of which is incorporated herein by reference.

Oftentimes, a compound of interest (analyte) in a substance is not detected directly but indirectly, by first reacting the analyte with another chemical or set of chemicals proximal to or in contact with an IDA. The reaction produces an electroactive reaction product that is electrochemically detectable and quantifiable by applying a potential difference between the counter and working electrodes and measuring the magnitude of the current produced. This allows measurement of the amount of electroactive reaction product generated by the first reaction, and correlation of that measurement to the amount of analyte in the sample substance.

An example of such a method involves the catalytic use of an enzyme, and is sometimes referred to as enzymatic amperometry. These methods can use an interdigitated array of electrodes coated with a chemical coating that contains a chemical compound reactive to produce an electroactive reaction product. (The chemical compound reactive to produce an electroactive reaction product is sometimes referred to herein as a "mediator.") Upon contacting the coating with a sample that contains an analyte, analyte reacts with chemical compounds of the coating to generate electroactive reaction product. This electroactive reaction product can be electronically detected, measured, or quantified, by applying a potential difference between the electrodes and measuring the current generated by the electrooxidation of the mediator at the working electrode. By calibrating the system's behavior using known substances and concentrations, the electrical behavior of the system in the presence of a sample substance of unknown composition can be determined by comparison to the calibration data.

The sensor of the invention may be used in amperometric applications, e.g., enzymatic amperometric applications, if disposed on the array is a coating of useful chemistry, including e.g., an enzyme and a mediator. When a sample containing an analyte is contracted with the coating, the analyte, enzyme, and the mediator participate in a reaction, wherein the mediator is either reduced (receives at least one electron) or is oxidized (donates at least one electron). Usually, in this reaction, the analyte is oxidized and the mediator is reduced. After this reaction is complete, an electrical potential difference can be applied between the electrodes. The amount of reducible species and the applied potential difference must be sufficient to cause diffusion-limited electrooxidation of the reduced form of the mediator at the surface of the working electrode. The IDA electrode configuration of the sensor places the working electrode fingers in close proximity to counter electrode fingers. Mediator electrooxidized at the working electrode can therefore diffuse rapidly to the adjacent counter electrode via radial diffusion where it is once again reduced. Likewise, oxidized mediator reduced at the counter electrode can migrate to the working electrode for electrooxidation to the oxidized form. This migration between the fingers produces a constant or "steady state" current between the electrodes. After a short time delay, this steady state current is measured and correlated to the amount of analyte in the sample.

The chemistries of the first and second reactions can be of any nature effective to produce the electroactive reaction product of the first reaction, to detect or quantify the electroactive reaction product during the second reaction, and to allow correlation of the amount of electroactive reaction product with the presence or concentration of analyte in the original sample.

In general, a typical first reaction can be an oxidation/reduction sequence, preferably occurring without the need for a chemical potential across the electrodes. It can be desirable for this reaction to favor maximum, preferably complete conversion of the analyte, and to proceed as quickly as possible. Often this reaction is catalyzed, e.g., enzymatically. Such reaction schemes and their application to enzymatic amperometry are known. See, e.g., U.S. Pat. No. 5,128,015; European Patent Specification EP 0 406 304 B1; and Aoki, Koichi, *Quantitative Analysis of Reversible Diffusion-Controlled Currents of Redox Soluble Species at Interdigitated Array Electrodes Under Steady-State Conditions*, J. Electroanal. Chem. 256 (1988) 269–282. An example of a useful reaction scheme can be the reaction of a component of a bodily fluid, e.g., glucose, with an enzyme and a cofactor, in the presence of a mediator, e.g., an oxidizer, to produce an electroactive reaction product.

The chemistry of a first reaction scheme of any chosen electrochemical detection method can be chosen in light of various chemical factors relating to the system, including the identity of the analyte and of the sample substance. Even then, for a given analyte or substance, various different reactive components may be useful in terms of a catalyst (often, a variety of enzymes will be useful), co-reactants (e.g., a variety of mediators may be useful), and cofactors (if needed, a variety may be useful). Many such reaction schemes and their reactive components and reaction products are known, and examples of a few different enzymes include those listed in Table 1.

| Analyte | Enzymes | Redox Mediator (Oxidized Form) | Additional Mediator |
|---|---|---|---|
| Glucose | Glucose dehydrogenase and Diaphorase | Ferricyanide, osmium (III)-(bipyridyl)-2-imidazolyl-chloride, Meldola blue, $[Ru(NH_3)_5MeIm]Cl_3$ $[OS(III)(NH_3)_5pyz]_2(SO_4)_3$, NITROSO analine derivatives | |
| Glucose | Glucose oxidase | (see above) | |
| Cholesterol | Cholesterol esterase and Cholesterol oxidase | (see glucose) | 2,6-Dimethyl-1,4-Benzoquinone, 2,5-Dichloro-1,4-benzoquinone, or phenazine ethosulfate |
| HDL Cholesterol | Cholesterol esterease and Cholesterol oxidase | (see glucose) | 2,6-Dimethyl-1,4-Benzoquinone, 2,5-Dichloro-1,4-benzoquinone, or phenazine ethosulfate |
| Triglycerides | Lipoprotein lipase, Glycerol kinase, Glycerol-3-phosphate oxidase | (see glucose) | Phenazine methosultate, phenazine ethosulfate. |
| Triglycerides | Lipoprotein lipase, Glycerol kinase, Glycerol-3-phosphate dehydrogenase and Diaphorase | (see glucose) | Phenazine methosultate, phenazine ethosulfate. |
| Lactate | Lactate oxidase | (see glucose) | 2,5-Dichloro-1,4-benzoquinone |
| Lactate | Lactate dehydrogenase and Diaphorase | (see glucose) | |
| Lactate Dehydrogenase | Diaphorase | (see glucose) | |
| Pyruvate | Pyruvate oxidase | (see glucose) | |
| Alcohol | Alcohol oxidase | (see glucose) | |
| Alcohol | Alcohol dehydrogenase and Diaphorase | (see glucose) | |

-continued

| Analyte | Enzymes | Redox Mediator (Oxidized Form) | Additional Mediator |
|---|---|---|---|
| Uric acid | Uricase | (see glucose) | |
| 3-Hydroxy-butric acid (ketone bodies) | 3-Hydroxybutyrate dehydrogenase and Diaphorase | (see glucose) | |

A mediator can be any chemical species (generally electroactive), which can participate in a reaction scheme involving an enzyme, an analyte, and optionally a cofactor (and reaction products thereof), to produce a detectable electroactive reaction product. Typically, participation of the mediator in this reaction involves a change in its oxidation state (e.g., a reduction), upon interaction with any one of the analyte, the enzyme, or a cofactor, or a species that is a reaction product of one of these (e.g., a cofactor reacted to a different oxidation state). A variety of mediators exhibit suitable electrochemical behavior. A mediator can preferably also be stable in its oxidized form; may optionally exhibit reversible redox electrochemistry; can preferably exhibit good solubility in aqueous solutions; and preferably reacts rapidly to produce an electroactive reaction product. Examples of suitable mediators include benzoquinone, medula blue, other transition metal complexes, potassium ferricyanide, and nitrosoanalines, see U.S. Pat. No. 5,286,362. See also Table 1.

To describe an example of an oxidation/reduction reaction scheme that is known to be useful for detecting glucose in human blood, a sample containing glucose can react with an enzyme (e.g., Glucose-Dye-Oxidoreductase (Gluc-Dor)) and optionally a cofactor, (e.g., pyrrolo-quinoline-quinone), in the presence a redox mediator (e.g., benzoquinone, ferricyanide, or nitrosoanaline derivatives), to produce the oxidized form of the analyte, gluconolactone, and the reduced form of the redox mediator. See U.S. Pat. No. 5,128,015. Other examples of reaction schemes are known, and are typically used in methods designed to detect a specific analyte, e.g., cholesterol, urea, etc.

After the reaction is complete, a power source (e.g., battery) applies a potential difference between the electrodes. When the potential difference is applied, the amount of oxidized form of the redox mediator at the counter electrode and the potential difference must be sufficient to cause diffusion-limited electrooxidation of the reduced form of the redox mediator at the working electrode surface. In this embodiment, the close proximity of the counter and working electrode fingers in the IDA electrode configuration aids in the fast radial diffusion of the reduced and oxidized redox mediator between the electrodes. Recycling of the mediator between the electrodes and their subsequent oxidation and reduction on the electrodes generates a constant or "steady state" assay current. This steady state assay current is measured by a current measuring meter.

The measured current may be accurately correlated to the concentration of analyte in the sample when the following requirements are satisfied:

1) the rate of oxidation of the reduced form of the redox mediator is governed by the rate of diffusion of the reduced form of the redox mediator to the surface of the working electrode; and 2) the current produced is limited by the oxidation of the reduced form of the redox mediator at the surface of the working electrode.

In the preferred embodiment, these requirements are satisfied by employing a readily reversible mediator and by using a mixture of amounts of mediator and other components of the chemical layer to ensure that the current produced during diffusion limited electrooxidation is limited by the oxidation of the reduced form of the mediator at the working electrode surface. For current produced during electrooxidation to be limited by the oxidation of the reduced form of the mediator at the working electrode surface, the amount of reducible species at the surface of the counter electrode must always exceed the amount of the reduced form of the redox mediator at the surface of the working electrode.

An example of a reaction scheme relates to the detection of glucose using ferricyanide and Glucose-Dye-Oxidoreductase (Glur-Dor). The electroactive reaction product of the enzymatic reaction between glucose and the enzyme is the reduced mediator, ferrocyanide. The ferrocyanide is electrooxidized at the working electrode back to ferricyanide. One mole of oxidized redox mediator is reduced at the counter electrode for every mole of reduced redox mediator oxidized at the working electrode. Ferricyanide electrooxidized at the working electrode, diffuses to the counter electrode, and the ferrocyanide produced at the counter electrode can rapidly diffuse to the working electrode where it is again oxidized. A "quasi-steady state" concentration gradient is established between the counter and working electrode pairs resulting in generation of a constant quasi-steady state current at the working electrode.

The magnitude of the current, preferably as measured at a quasi-steady-state condition, can be correlated to the amount of electroactive reaction product present in the coating, and consequently, to the amount of analyte in the sample.

The chemical coating should allow diffusion of analyte into the coating, followed by reactions as described. The coating can include materials which can contain the reactive chemical components, which allow reaction between the components to product an electroactive reaction product, which allow necessary diffusion of chemical components, and which can support a current passing through the coating based on the concentration of electroactive reaction product. Typically, the coating can be made up of a binder that contains a set of chemicals which react to produce an electroactive reaction product. The chemicals generally include a mediator and necessary enzymes and cofactors. Such a coating can also contain a variety of additional components to make the coating operative and suitable for processing, including specific components listed above as well as surfactants, film formers, adhesive agents, thickeners, detergents, and other ingredients and additives that will be understood by an artisan skilled in the electrochemical sensor art.

The binder can provide integrity of the coating while allowing diffusion of the different components of the reaction scheme, reaction between the reactive components, and movement of reactive components and products sufficient to produce a quasi-steady-state concentration gradient of mediator and electroactive reaction product and thereby establish a stable or quasi-steady-state current between the electrode pairs. Exemplary binders can include gelatin, carrageenan, methylcellulose, polyvinyl alcohol, polyvinylpyrrolidone, alignate, polyethylene oxide, etc.

A sensor according to the invention can be understood to include a micro-electrode disposed on a flexible substrate, optionally including a chemical coating, and further including any immediate appurtenance necessary to use the sensor in an electronic system or apparatus (e.g., test stand) designed, for example, for use in an electrochemical detection method. A sensor can include the interdigitated array disposed on a flexible substrate, with additional components to independently connect each of the separate electrodes to a different voltage, e.g., electrical connectors, leads, or pads. In some circumstances, the sensor may include a reference electrode provided on the same or a different substrate and electrically insulated from the interdigitated array. The sensor may also include components to direct flow of a sample substance into contact with the IDA, e.g., a vessel, channel, microchannel, or capillary. A particularly preferred embodiment of the sensor includes a microchannel or capillary, most preferably a capillary, which directs flow of a sample substance into the reaction chamber and over the IDA (e.g., a coated IDA).

A capillary can be included in a sensor to facilitate analysis of a small volume of a sample substance by precisely directing the flow of a volume of sample over the IDA, preferably in a short period of time. Analysis of relatively small volumes of a sample substance can be accomplished, at least in part, due to the signal amplification features of the IDA.

Preferred dimensions of a capillary for what can be referred to as a "low volume sensor configuration," can be in the range of 0.025 mm to 0.2 mm (depth), preferably about 0.125 mm (depth), ×1 mm (width)×3 mm (length), resulting in a capillary chamber requiring a relatively small volume of sample, e.g., less than 400 nanoliters (nL). The volume of the chamber can preferably be such that a low volume sample of a substance can be directed into or through the chamber for analysis. Chamber volumes will vary depending on the type of analyte being studied, and even its concentration of an analyte. (Blood samples of different hematocrits will dispense differently into a capillary.) Exemplary chamber volumes can be in the range from about 100 to 300 nanoliters for glucose analysis in interstitial fluid, and from about 250 to 400 nanoliters for glucose analysis applications in the whole blood. In the most preferred embodiments of the sensor, including a capillary, the capillary may have a vent to facilitate flow of a sample substance into the capillary chamber by equalizing pressure between the interior and exterior of the chamber.

The sensor of the invention can include these and other features, and, especially if an embodiment is disposable, can be referred to as a "test strip" or a "test cell." The term "disposable" refers to sensors designed or sold for a single use, after which they are to be discarded or otherwise stored for later disposal.

Capillaries may be fabricated as a component of a sensor, using photolithographic methods, e.g., as described infra.

Figure 2:
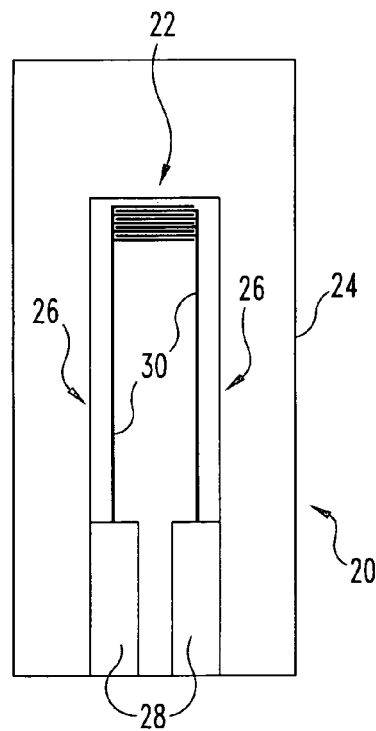
FIGS. 2 and 2A each show a top view of a sensor of the invention.
Figure 2A:
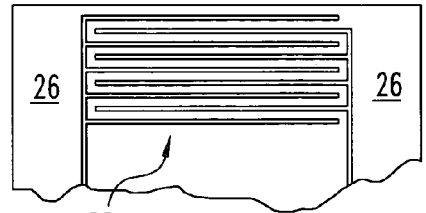

An example of a sensor construction is shown in FIG. 2, according to the preferred embodiment. The figure shows sensor 20, including an interdigitated array of electrodes 22 disposed on flexible substrate 24. The electrodes are connected to electrically-conductive connectors 26 which include portions 28 that can be identified as pads, located on the surface of the flexible substrate, where they are available to be contacted to an external electronic circuit such as a testing apparatus. The connectors also include connector portions 30, which connect electrode elements at the array to the pads, and which may typically be covered by an insulating layer. FIG. 2a shows a close-up of array 22, showing that electrodes attached to each of connectors 26 are arranged in an inter digitated fashion (as shown in FIG. 1).

Figure 3:
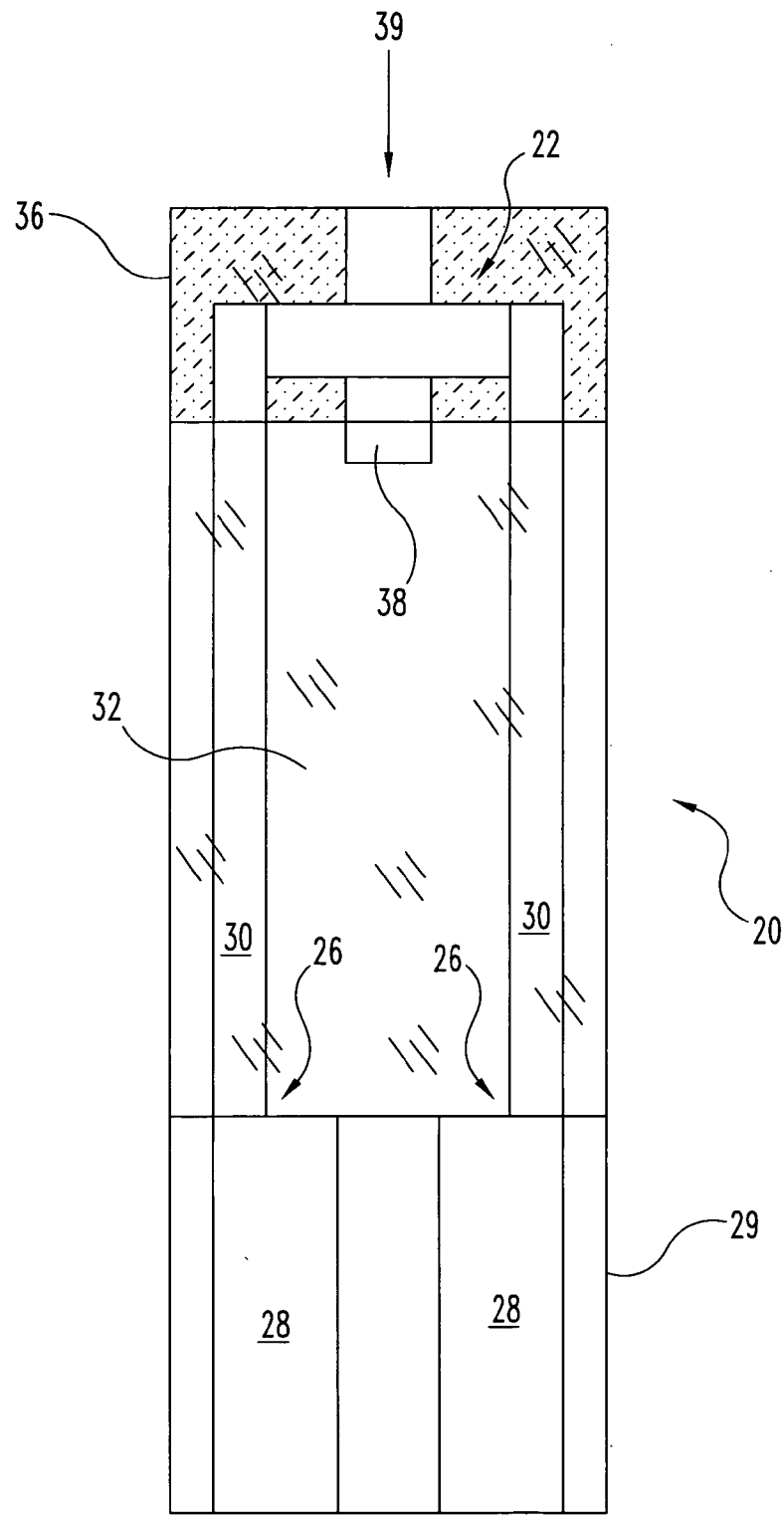
FIG. 3 shows a top view of a sensor of the invention.
Figure 4:
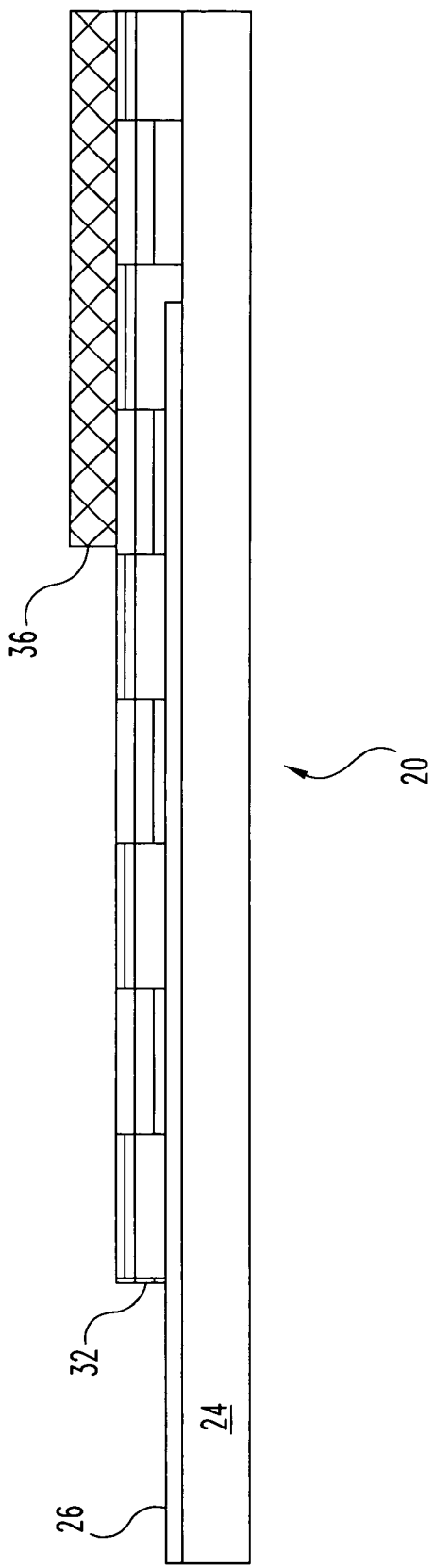
FIG. 4 shows a side view of a sensor of the invention.
Figure 5:
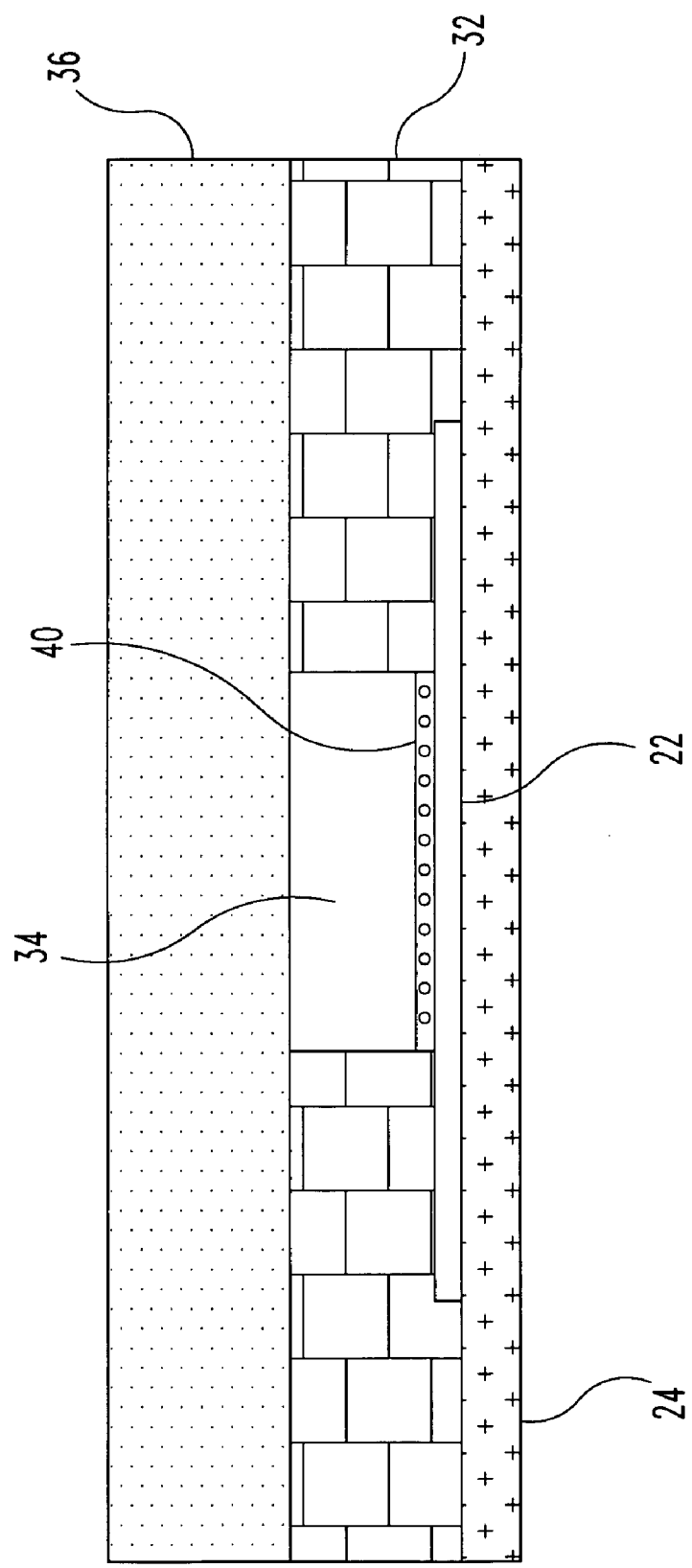
FIG. 5 shows a side view of a sensor of the invention.

FIG. 3 shows different details of a sensor of the invention. FIG. 3 shows sensor 20 comprising flexible substrate 24, an array of interdigitated electrodes 22, and connectors and pads. Non-conductive layer 32 is disposed over the substrate and connector portions 30 of the connectors 26, over portions of the array 22, and not over a rectangular capillary portion including some of the substrate and an intersection of array 22; this rectangular portion defines capillary chamber 34. (A chemical coating, not shown in this figure, is preferably disposed over the array, within the capillary chamber.) Foil 36 covers a rectangular portion of the sensor, including portions of the non-conductive layer 32, and a portion of capillary chamber 34, except for air vent 38. This embodiment is shown from one side in FIG. 4, and from another side in FIG. 5. FIG. 5 specifically illustrates substrate 24, array 22, non-conductive layer 32, which defines chamber 34, and foil 36. FIG. 5 additionally includes coating 40 disposed on array 22, within the capillary.

Figure 6:
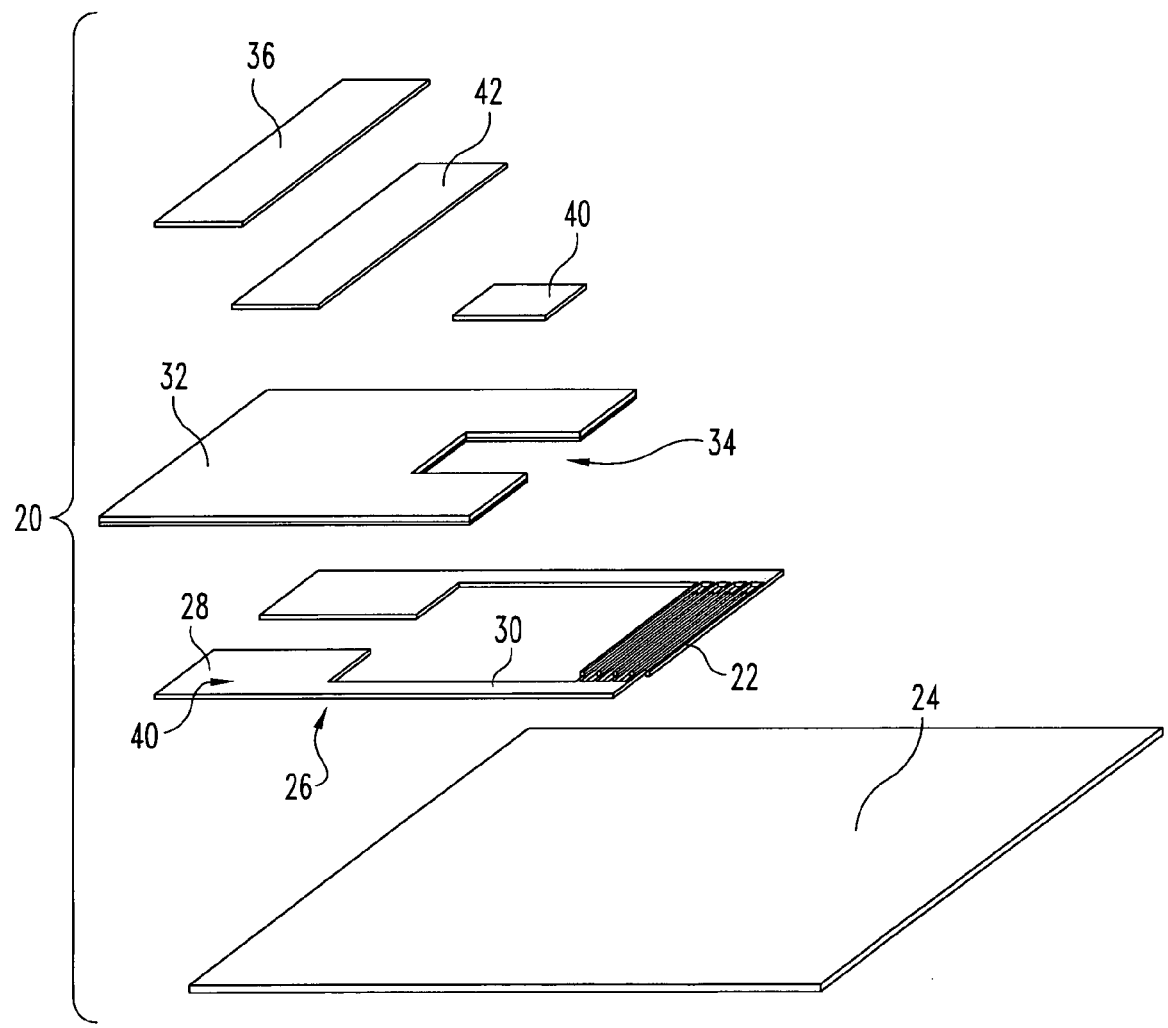
FIG. 6 shows a perspective view of a dissembled sensor of the invention.

FIG. 6 illustrates an exploded view of a sensor of the invention. The sensor 20 includes flexible substrate 24; a conductive film 40 patterned with an interdigitated array of electrodes 22 and connectors 26 which include pad portions 28 and connecting portions 30, an insulating material 32 which defines the depth and dimensions of capillary chamber 34, a chemical coating 40 disposed in the capillary chamber 34, and top foil 36 coated with a hydrophilic adhesive layer 42.

The array of the invention, in various embodiments such as a sensor, can be used in electrochemical detection methods, including those using the principles and specific methods described above, and others. Such methods employ the array disposed on a flexible substrate, preferably further including a chemical coating contacting the array.

Upon contacting the coating with a sample containing analyte, analyte generally diffuses into the coating at a rate dependant on factors such as the chemical composition of the coating and the chemical identity of the analyte. Generally, the chemical coating will be at least partly solubilized or hydrated by the sample substance. For a method to provide the quickest read time (the time following contact with a substance sample, when a reading of the concentration of analyte in the substance is available), it is desirable that the analyte diffuse quickly into the coating, and thereafter quickly and completely react to produce an electroactive reaction product. The period during which this occurs can be reduced by operating on a relatively small volume of sample, and by using a sensor having a relatively small amount of chemical coating to be solubilized or hydrated.

The time from when the substance containing the analyte is contacted with the chemical coating until an assay potential is applied to the array, and during which the analyte diffuses into the coating and reacts to produce an electroactive reaction product, can be referred to as the "delay period". This period can be any amount of time necessary for the above occurrences to transpire, is preferably minimized, and in some embodiments can be less than about 10 seconds, preferably in the range from about 2 to 6 seconds.

After a delay period, the electric properties of the coating can be measured. By chronoamperometric methods, or by potentiometric methods, as will be appreciated by the skilled artisan, either the current or the applied potential can be controlled, and any of the related current, resistance, or voltage can be measured and correlated to amounts of electroactive reaction product and analyte. The magnitude of the current, or alternatively potential difference or the resistance of the chemical coating, can be measured using an external circuit connected to the sensor electrodes.

As an example, according to chronoamperometric methods, a potential ("assay potential") can be applied across the electrodes, inducing a current ("assay current") to flow through the coating. The potential should be enough to cause reduction or oxidation of the redox products formed in the first step of a binary reaction scheme (e.g., as described above), but should not be sufficient to cause other electrochemical reactions or to otherwise cause significant current to flow through the coating. The assay potential can be chosen depending on the redox mediator chosen, factors relating to the electrochemical detection method, the electrochemical system and reaction scheme, and the general capabilities of the sensor. A typical potential can be in the range of a few to several hundred millivolts, e.g., from about 100 to 500, preferably 200 to 400 millivolts.

A measured current can initially exhibit a spike to a relatively elevated level, and can then descend to a steady-state current based on a quasi-steady-state concentration gradients and a recycle reaction loop of the mediator and electroactive reaction product. Preferably, the magnitude of the current can be measured at a time when current flowing through this system has approached a plateau, based on quasi-steady-state concentration gradients. The period of time starting with application of the assay potential and lasting to the plateau or near-steady-state current can be referred to as the "assay period." Steady-state assay currents can occur within various such time periods, depending upon the reaction scheme, the chemistries of its components, etc. In the practice of the invention, assay periods of less than one minute are preferred, e.g., less than 30 seconds, and assay periods of even shorter duration, less than 10 seconds, are most preferred. The assay profile (the profile of the assay current over time) can be to some extent controlled by changing the spacing between electrode elements in the array; increased spacing between electrode elements can result in a longer time interval between assay potential application and formation of the steady state assay currents.

Assay currents exhibited by exemplary sensors of the invention can be any current that will function in an electrochemical detection method. For the sensors of the invention, any useful current can be used, preferably with a range between a lower end in the nanoamp range (e.g., between 20 to 25 nanoamps) up to the microamp range e.g., 100 microamps, being an exemplary working range, e.g., at the steady state current plateau. Typical steady state assay currents can be in the range from below one microamp up to around 100 microamp, preferably from about 0.5 to about 25 microamps. In an embodiment of the invention useful for detecting glucose content of a blood sample, the current response (steady state assay current) in this range has been found to be linear with respect to the concentration of glucose in the sample, particularly for glucose concentrations in the range from about 0 to 600 milligrams per deciliter (mg/dL).

Sensors of the invention may be used in cooperation with electronic or computerized systems and apparatuses, and in combination with methods for identifying analytes and measuring concentration of analytes within a substance sample. For example, a sensor can be used with a VXI or Biopotentiostat test stand built from components purchased from National Instrument Corp., Austin, Tex. In this context, the method of the invention can be practiced with a delay period of around 3 seconds, an assay potential of about 300 millivolts, and an assay period which, although variable, can preferably be in the range from about 1.5 to 2 seconds after applying the assay potential.

The sensors can be used in such a method to detect and quantify the concentration of an analyte within a sample substance. The analyte can be chosen from various chemical compounds present within any of a large variety of substances, generally fluids. Examples of analytes include glucose, cholesterol, urea, and the like. Examples of substances containing the analyte include bodily fluids such as blood, urine, and interstitial fluid; water such as environmental water, ground water, waste water, etc.

In some embodiments of the invention, analytes can be detected at very low concentrations, for example glucose can be measured at concentrations as low as 0.5 mg/dL (5 ppm) in blood using ferricyanide as the mediator.

The use of an array or sensor of the invention offers certain practical advantages. For instance, a flexible substrate can be used in combination with relatively larger-dimensioned electrodes, including electrode components of increased size (e.g., width) as well as increased spacing between them. Lower sample volumes can independently decrease the time of the delay period. A shorter delay period in combination with an expedited formation of a quasi-steady-state region of the assay current produces a quicker read time. In the practice of the invention, read times of less than 10 seconds have been achieved, with a read times in the range from about 4 and 5 seconds being preferred.

Test cells and test strips according to the invention allow for controlled volumes of blood to be analyzed without pre-measuring. Insertion of the test cell into an electronic or computer-controlled apparatus (referred to generally as a test stand) permits automatic functioning and timing of the reaction and analysis of the sample. This allows for patient self-testing with a very high degree of precision and accuracy. The method, the sensor or test cell, and the apparatus, are designed to provide self-monitoring by a patient of important bodily fluids, e.g., blood glucose levels. The sensor is used to control the sample volume and reaction media, to provide precise, accurate, and reproducible analysis. Preferably, disposable test strips or test cells can be used in combination with a portable electrochemical testing meter.

The preferred embodiment of the present invention uses a micro-electrode array consisting of interdigitated microband electrodes as described above. Although this arrangement leads to the aforementioned re-cycling of redox products between narrowly separated working and counter electrodes, this is not a strict requirement for successful practice of the invention. An alternative embodiment is the provision of an array of more general micro-electrodes to act as the working electrode structure. These may be microbands that are not interdigitated with the counter electrode, or micro-disks, also not closely spaced with the counter electrode. In this case the width or diameter of the working electrode bands or disks should be of such a dimension as to allow for some degree of radial or spherical diffusion to the working electrode surfaces. Typically, this dimension should be in the range of 5 to 50 µm, and most preferably 10 to 50 µm for the case of aqueous systems such as encountered with a sensor used for the assay of biological fluids. In both cases the counter electrode is provided at a distance from the working array that is generally larger than the smallest dimension of the working electrodes.

In these embodiments, specific recycling of redox species between the working and counter electrodes is not observed in the same way as in other described embodiments, and assay current magnitudes are consequently reduced. Nevertheless, the effect of radial or spherical diffusion to working micro-electrode structures can still be observed as current densities that are greater than that predicted from linear diffusion alone. Although reduced in magnitude, and not approaching quasi-steady-state as displayed by the preferred embodiments, it is still possible to measure dose responses to the analyte in question (e.g. glucose) when the same reagent as described above is disposed on the micro-electrode array.

Micro-electrode arrays of the invention can be disposed onto a flexible substrate using various methods useful for disposing electronic components onto substrates, especially flexible substrates. A variety of such methods are generally known for fabrication of different types of circuitry, and include specific techniques of dry-coating, lamination, spin-coating, etching, and laser ablation. One or more of the following generalized methods may be specifically useful to prepare microelectrode arrays according to the invention.

One method of preparing a micro-electrode array as described herein, e.g., an IDA, is by the use of laser ablation techniques. Examples of the use of these techniques in preparing electrodes for biosensors are described in U.S. patent application Ser. No. 09/866,030, "Biosensors with Laser Ablation Electrodes with a Continuous Coverlay Channel" filed May 25, 2001, and in U.S. patent application Ser. No. 09/411,940, entitled "Laser Defined Features for Patterned Laminates and Electrode," filed Oct. 4, 1999, both disclosures incorporated herein by reference.

In general, laser ablative techniques use a laser to cut or mold a material. According to the invention, micro-electrodes can be prepared using ablative techniques, e.g., by ablating a multi-layer composition that includes an insulating material and a conductive material, e.g., a metallic laminate of a metal layer coated on or laminated to an insulating material. The metallic layer may contain pure metals or alloys, or other materials which are metallic conductors. Examples include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements. Preferably, the metallic layer includes gold, platinum, palladium, iridium, or alloys of these metals, since such noble metals and their alloys are unreactive in biological systems. The metallic layer may be any thickness but preferably is 10 nm to 80 nm, more preferably 20 nm to 50 nm.

In the laser ablation process, the metallic layer may be ablated into a pattern of micro-electrodes. The patterned layer may additionally be coated or plated with additional metal layers. For example, the metallic layer may be copper, which is then ablated with a laser, into an electrode pattern. The copper may be plated with a titanium/tungsten layer, and then a gold layer, to form desired micro-electrodes. Preferably, however, in some embodiments, only a single layer of gold is used. One example of a useful metallic laminate is a polyester or other flexible substrate such as a Kaladex film, coated with a layer of gold, preferably about 5 mils in thickness.

The conductive material is ablated with the laser to leave a micro-electrode array. Any laser system capable of ablation of the conductive material will be useful. Such laser systems are well known and commercially available. Examples include excimer lasers, with a pattern of ablation controlled by lenses, mirrors, or masks. A specific example of such a system is the LPX-400, LPX-300, or LPX-200, both from LPKF LASER ELECTRONIC, GMBH of Garbsen, Germany.

One specific example of a process for laser ablation is as follows. Sheets of sensor traces are fabricated in a MicrolineLaser 200-4 laser system (from LPKF). The system chamber includes a vacuum platen atop of a LPKF-HS precision positioning X,Y table, laser mirrors and optics, and a quartz/chromium photomask (International Phototool Company, Colorado Springs, Colo.) with the sensor components subdivided into rectangular fields on the mask. Photomask positioning, X,Y table movement and laser energy are computer controlled. Sheets of metal laminate 22 cm×22 cm in dimension are placed into the chamber onto the vacuum table. The table moves to the starting position and the Kr/F excimer laser (248 nm) is focused through the first field of the photomask onto the metal laminate. Laser light passing through the clear areas of the photomask field ablates the metal from the metal laminate. Chromium coated areas of the photomask block the laser light and prevent ablation in those areas, resulting in a metallized sensor structure on the laminate film surface. The complete structure of the sensor traces may require additional ablation steps through various fields on the photomask.

Another method of preparing the described micro-electrode array is the use of flex circuit photolithography. Flex circuit photolithography methods are well known. Two general methods of fabricating flexible circuits include the "additive" method and the "subtractive" method. With the additive method, an IDA and associated circuitry can be built up on top of a non-conductive flexible substrate. With the subtractive method, a non-conductive flexible substrate can be laminated with a conductive material (e.g., a copper foil) and conductive material is patterned using conventional photolithographic and wet chemical etching techniques. Some conventional processing steps include cleaning a substrate or intermediate; depositing conductive materials onto a substrate, e.g., by vapor deposition, electrodeposition, or vacuum plasma sputtering; depositing non-conductive or processing materials onto a substrate such as a photoresist material; masking and developing a photoresist material in a pattern defining an electrode; and removing excess developed or non-developed materials such as photoresist materials or conductive materials, to leave behind a desired arrangement of electrically conductive and insulating materials.

According to one series of steps in flex circuit photolithography, a substrate is prepared by cleaning, and a conductive material can be applied as a film to the substrate. Preferred thicknesses of a conductive layer (e.g., a gold conductive layer) can be in the range from about 500 to 1000 angstroms. It may be desirable to include a seed layer such as titanium or chromium between the conductive layer and the substrate, to improve adhesion. A preferred conductive material can be gold, and a preferred method of application can be sputtering, which has been found to provide very good adhesion.

A photoresist material can be applied to the conductive layer. Such photoresist materials are commercially known and available, with one example being Riston® CM206, from duPont. The thickness of the photoresist can be chosen to advantageously affect the resolution of the feature sizes of the electrode components. Improved resolution generally provides for better quality arrays, with fewer failures. There has been found a 1:1 relationship between the resolution of the smallest feature size achievable, and the thickness of the dry film photoresist, with thinner photoresist films providing better resolution (a thickness of about 0.6 mils generally allows a feature spacing or width of 0.6 mils). Riston® CM206, in the form of a 0.6 mil thick roll of film, can be a preferred photoresist because it can be capable of resolving features, i.e., lines and spaces, on a lower micron scale, e.g., in the range of 0.6 mils (15 microns) or lower. A photoresist layer often requires heating. Riston® CM206 does not require prebaking. The material is a dry film photoresist and is applied to the gold substrate using a heated laminated roller system. Once laminated, the material is ready for processing (exposure to UV light, and development).

The laminated film can be cut to a convenient size, e.g., one foot by one foot, and a pattern defining a microelectrode array can be cured or crosslinked. This can generally be accomplished by conventional methods, e.g., using a mask pattern and exposing the array pattern to ultraviolet light, crosslinking the photoresist in the pattern of the array. Unexposed, uncrosslinked, photoresist can be developed away using a developing agent, which will typically be particular to the photoresist composition (e.g., lithium carbonate is one developing agent; see the manufacturer's instructions). At the end of this step, the substrate will have an undisturbed layer of the conductive material coated thereon, with a photoresist design defining the pattern of the array laid out on the conductive layer. This allows for unprotected conductive material to be etched away using an etchant (e.g., $KI/I_2$), to produce the IDA pattern in the conductive material. The remaining photoresist can then be removed.

Once an array is prepared, e.g., by laser ablative methods, using laminated dry photoresist, spin coating, etching, or other techniques, further processing of the micro-electrode array can be used to incorporate the array into a useful electronic device such as a biosensor. Preferably, additional materials can be disposed onto the array to form, for example, a spacer or insulating layer, optionally including a well or a microchannel or capillary. A well refers to a space over an array that defines the array. A microchannel or capillary more specifically refers to a space or channel that is defined over the array to allow the flow of a fluid over the array. The material used to define the microchannel or capillary can be any of a variety of materials useful insulating or spacing materials, sometimes referred to as "coverlay" materials, as well as other material useful for processing with the described fabrication methods. An example is Pyralux coverlay, and similar materials would also be useful.

Methods useful to place a microchannel or capillary onto the array include methods of mechanical lamination and mechanical removal of material to form a channel or capillary. One method would include a first step of mechanically "punching" (e.g., die punching) the coverlay material to cut away one or multiple portions of the material in the form of wells or channels, and then laminating the material to one or a number of sensors such that the channel is present over the array. Another method includes those types of methods generally referred to as "kiss die cutting" or "kiss cutting," which may be used to cut a well or channel in a coverlay layer, and then the coverlay material may be laminated onto the substrate with the well or channel over the array.

A different example that includes a die punching method is as follows. A spacer foil was prepared by coating an adhesive, Fastbond™ 30-NF Contact Adhesive to a wet thickness of 25 μm onto a 5 mil polyester film such as that sold under the trademark Melinex® S (DuPont Polyester films, Wilmington Del.) using a wire bar coater from Thomas Scientific of Swedesboro, N.J. The coated top foil was dried for 2 minutes at 50 C in a horizontal air flow oven. The dried adhesive on the sheet was covered with either silicon or teflon release liner. Capillary channels and electrode contact well patterns were kiss cut into the sheet using an Aristomat 1310 ditigal die cutting system (Aristo Graphic Systeme GmbH & Co., Hambrug Germany). The spacer sheet can then be registered and laminated to an ablated sheet of sensor traces, as described above. Channels and electrode contact wells can also be produced using die punching processes in a similar fashion.

Another specific method by which to dispose a capillary or microchannel onto a micro-electrode array would be by methods of flex circuit photolithography. Accordingly, a photoimageable coverlay material such as Vacrel 8140®, (a dry film coverlay can be preferred) can be vacuum laminated onto the gold/plastic laminate. Multiple layers of various chosen thicknesses can be added to control the depth of the capillary chamber (see infra). The sheet can be exposed to ultraviolet light through a mask pattern to define capillary chambers. The exposed laminated sheet is developed by conventional methods, e.g., using 1% $K_2CO_3$, to remove crosslinked photopolymer coverlay material and leave behind components of a capillary. The sheet is generally thereafter cured, e.g., at 160 C for 1 hour.

In fabricating the capillary, the depth of the chamber can be controlled by choosing the coverlay material or materials used, according to thickness. Vacrel 8140® ( film has a thickness of 2, 3, or 4 mil (100 μm). Pyralux PC® 1000, 1500, have 2000 have maxium thicknesses of 2.5 mils (63.5 μm), so double layer lamination gives a chamber depth of 127 μm. Pyralux 1010 has a thickness of 1 mil or 25.4 μm. Capillaries with depths of greater than or equal to 100 μm have been found to allow fast fill of blood with hematocrits from 20 to 70% to reliably flow into the chamber. Capillary depths of less than 100 microns to 25 microns can be used for other biological fluids such as serum, plasma, intersticial fluid, and the like.

A chemical coating may also be disposed onto the array. First, however, it may be beneficial to clean the sensors. By one cleaning method, a sheet of sensors as described can be plasma cleaned in a Branson/IPC Plasma Cleaner according to steps such as the following: (1) $O_2$ for 1 minute at 800 watts; (2) $O_2$/Argon(Ar) (70/30) for 3 minutes at 220 watts; (3) Ar for 2 minutes at 150 watts.

A chemical coating, as described, may be dispensed onto the array, e.g., into each capillary chamber and over the interdigitated arrays, by known methods. The method of dispensing is preferably capable of reproducibly and consistently delivering very small volumes of a chemical composition, onto the array—e.g., volumes in the range of hundreds of nanoliters, e.g., 625 nanoliters. As an example, such a coating may be dispensed using known syringe and metering techniques and apparatuses, including dispensing systems sold under the trade name Microdot (from Astro Dispense Systems, a DCI Company of Franklin, Mass. 02038-9908) and systems sold by BioDot Inc., Irvine, Calif. The coatings may then be dried of solvent. The inlet ports are opened, and a top foil coated with a hydrophilic adhesive is applied over the capillary chamber using heat and pressure to form the completed three-dimensional sensor structure.

The top foil can be any continuous film capable of defining one side of the capillary, and preferably being capable of appropriate processing, e.g., as described herein. Exemplary materials for the foil can include plastic films such as polyethylene naphthalate (PEN), film type Kadalex 1000, 7 mil thick.

Any of a variety of hydrophilic adhesives can be used to bond the top foil to the sensor. Two part thermoset adhesives such as polyurethane mixtures and isocyanate mixtures can be used, e.g., 38-8668 (polyurethane) and 38-8569 (isocyanate) (95:5 wt./wt.) from National Starch and Chemical Co. of Bridgwater N.J., or, a two part epoxy systems such as that sold under the trademark Scotch Weld™ 2216 B/A (3M Adhesive Div., St. Paul Minn.), as well as contact adhesives such as that sold under the trademark Fastbond™ 30-NF Contact Adhesive, provided that they exhibit acceptable sealing properties to the crosslinked coverlay surface. A preferred adhesive was found to be a mixture of Fastbond™ 30-NF Contact Adhesive and the surfactant Triton™ X-100 (Union Carbide, Danbury Conn.), 93%:7% wt./wt.

EXAMPLES

The following describes a process useful for preparing a sensor according to the invention, comprising an interdigitated array disposed on a flexible substrate. According to the method, a gold film can be deposited onto 7 mil thick Kaladex® film using a planar DC magnetron sputtering process and equipment, from Techni-Met Inc., Windsor, Conn. The thickness of the gold film can range from 30 to 200 nm, with a preferred thickness being 100 nm. Seed layers of chromium or titanium can be sputtered between the plastic film and the gold to promote better adhesion of the gold to the plastic substrate, however, gold layers sputtered directly onto the plastic film can exhibit sufficient adhesion.

The interdigitated array and connectors can be fabricated using batch photolithography processes common to the flex circuit industry. Electrodes with combinations of finger width and spacing between fingers in the range of 21 to 50 µm were easily fabricated using these processes. A preferred configuration of the array was 21 total fingers (10 working electrode fingers and 11 counter electrode fingers), with finger dimensions of 25 microns (width) by 1 millimeter (length), with 21 micron spacing between the fingers.

After the gold was applied to the flexible substrate, a dry film photopolymer resist was laminated to the gold/plastic film. A dry film resist such as that sold under the trademark Riston® CM206 (duPont) was preferred. The Riston® CM206 photoresist was first wet laminated onto the gold surface of 12"×12" gold/plastic panels using a HRL-24 hot roll laminator (from duPont). The sealing temperature and lamination speed were 105° C. and 1 meter per minute. The laminated panel was placed in a Tamarack model 152R exposure system, from Tamarack Scientific Co., Inc., Anaheim, Calif. The release liner was removed from the top surface of the photoresist. A glass/emulsion photomask of the IDA configuration was produced by Advance Reproductions Corporation, North Andover, Mass. The emulsion side of the mask was treated with an antistick coating (Tribofilm Research Inc., Raleigh, N.C.), and was placed directly onto the photoresist surface of the panel. The laminated panel was exposed to ultraviolet light of 365 nm through the photomask using an exposure energy of 60 mJ/cm$^2$. Exposed photoresist was stripped from the panel in a rotary vertical lab processor (VLP-20), Circuit Chemistry Equipment, Golden Valley, Minn., using 1 % potassium carbonate, at room temperature, for 30 seconds using a nozzle pressure of 34 psi. Exposed gold on the sheet was then stripped using an etch bath containing a solution of: 4 parts I$_2$:1 part KI:40 parts water vol./vol.; and 0.04 gram Fluorad™ fluorochemical surfactant FC99, (3M, St. Paul, Minn.) per 100 gram solution, added to the bath to ensure wetting of the photoresist. Air was bubbled through the bath during the etch process to obtain uniform agitation of the bath mixture. The panel was rinsed with deionized water and residual Riston® CM206 was removed in a 3% KOH bath.

Sensor chambers were fabricated using dry film photoimageable coverlay materials such as that sold under the trademark Vacrel® 8140 (duPont) or Pyralux® PC series (duPont). The chamber dimensions can be accurately defined by flex circuit photolithography. Depth of the chamber was controlled by the thickness of the coverlay materials used, and whether single or multiple layers of the coverlay dry film were used. A preferred chamber depth was 125 microns (5 mil). This chamber depth was achieved by sequential lamination of different coverlay materials as follows: three mil thick Vacrel® 8130 was first laminated to the electrode side of the substrate using a HRL-24 (duPont) heated roll laminator at room temperature, using a roller speed of 1 meter per minute. The electrode panel was then vacuum laminated in a DVL-24 vacuum laminator (duPont) using settings of 120° F., 30 second vacuum dwell, and a 4 second pressure to remove entrapped air between the coverlay film and the electrode substrate. Two mil thick Vacrel 8120 was laminated next to the Vacrel® 8130 surface using the HRL-24 at room temperature, with a roller speed of 1 meter/min. The panel was then vacuum laminated again in the DVL-24 vacuum laminator using a 30 second vacuum dwell, 4 second pressure, to remove entrapped air between the two coverlay films.

The laminated electrode sheet was placed in the Tamarack 152R system and was exposed to ultraviolet light at 365 nm through the photomask for 22 seconds using an exposure intensity of 17 mW/cm$^2$. The artwork for the capillary chamber was a 1 millimeter by 4 millimeter rectangle centered over the electrode finger array and starting 1 millimeter below the fingers. The exposed coverlay was stripped from the panel to reveal the sensor chamber rectangle using the VLP-20 Circuit Chemistry Equipment) in 1% K$_2$CO$_3$, at 140° F., for 75 seconds using a nozzle pressure of 34 psi. The developed laminate structure was rinsed in deionized water, and then cured at 160° C. for 1 hour to thermally crosslink the coverlay material. This completed the construction of the sensor base.

The panel of the base sensors was plasma cleaned to remove residual photoresist and coverlay material from the exposed gold surface of the interdigitated array structure. The panel was placed in a barrel etcher, a Barnstead/IPC model P2100 from Metroline/IPC of Corona, Calif. The panel was first exposed to an oxygen plasma for 1 minute at 800 watts and 1.1 torr pressure to oxidize the panel surface. It was then etched in an oxygen/argon plasma mixture (70/30 vol./vol.) for 3 minutes, at 225 watts and 1.5 torr pressure, and was finally stripped in an argon plasma for 2 minutes, at 150 watts and 2 torr pressure.

The chemical coating was formulated for measurement of d-glucose in a human blood sample. The chemical coating was reactive with the sample in a manner effective to generate an electrical output signal indicative of the level of glucose in the sample. The coating included a mediator, enzymes, and a cofactor. The coating further comprised film forming agents and detergents conferring durability and providing hydrophilicity. The ingredients are listed in Table 1; unless stated otherwise, all concentrations refer to the concentration of a given substance in a wet-coating, prior to the deposition and drying of the coating onto the array.

The chemical coating was formulated from several sub-mixtures of components. A first mixture contained glycerophosphate buffer, from ICN Biomedicals Inc. Aurora, Ohio; Medium Viscosity Alginic acid, from Sigma Chemical Co., St. Louis, Mo.; Natrosol 250M, from Hercules Inc., Wilmington, Del.; and Triton® X-100, from Union Carbide, Danbury Conn. These components were added to a volume of distilled water sufficient to make a 250 gram solution of the buffer/polymer/surfactant (see Table 1). The solution was mixed overnight to allow complete hydration of the Natrosol and Alginic acid. The pH of the completed solution was adjusted to 6.9 to 7.0 with concentrated hydrochloric acid. This solution is known hereinafter as "Solution A."

A second solution prepared was a concentrated enzyme/cofactor matrix. 8.2 milligrams pyrrolo-quinoline-quinone (PQQ), Fluka, Milwaukee, Wis., was added to 25.85 grams of Solution A. The resulting mixture was sonicated until the PQQ was completely in solution. 1.1394 grams of the enzyme, Glucose-De-oxidoreductase (GlucDor), from Roche Molecular Biochemicals, Indianapolis, Ind., was added to the solution. The final mixture was rocked for 2 hours to allow formation of the GlucDor/PQQ holoenzyme. The completed solution will be referred to as "Solution B."

Potassium ferricyanide was added to the composition as follows: 4.4173 grams of potassium ferricyanide, from J. T. Baker, Phillipsburg, N.J., was added to 70.58 grams of Solution A. The resulting solution was mixed until the ferricyanide was completely in solution. The completed solution will be referred to as "Solution C."

The final coating composition was completed by combining 63 grams of Solution C to 25 grams Solution B. This composition was rocked in the dark for 1 hour to thoroughly mix.

TABLE 1

Formulation per 100 grams of coating

| Component | Concentration/ activity | Wet mass (g) | Dry mass/sensor (mg) |
|---|---|---|---|
| Distilled Water | | 88.487 | |
| Disodium Glycerophosphate | 150 mM pH 6.98 | 4.359 | 0.0287 |
| Trehalose | 1% wt/wt | 1.000 | 0.0066 |
| Natrosol | 0.3% wt/wt | 0.300 | 0.002 |
| Alginic acid Medium viscosity | 0.4% wt/wt | 0.400 | 0.0026 |
| Triton X-100 | 0.025% wt/wt | 0.025 | 0.00016 |
| Pyrrolo-quinoline-Quinone (PQQ) | 0.261 mM | 0.0082 | $5.3382 \times 10^{-5}$ |
| GlucDor Enzyme | 2034 u/mg | 1.1394 | 0.0075 15.23 (units) |
| Potassium Ferricyanide | 137 mM | 4.2814 | 0.0281 |

A preferred method for applying the chemistry matrix to the sensor chamber (IDA) is a discrete dispense of 500 nanoliters of the coating solution into the 1 millimeter×4 millimeter chamber using a microdispensing system such as that sold under the trademark of BioJet Quanti3000®, BioDot Inc., Irvine, Calif. The coating covered both the working and counter electrodes of the IDA. The coating was dried for 1.5 minutes at 45° C. in a horizontal air flow oven, VWR Scientific Products, Chicago Ill.

The hydrophilic top foil was prepared by coating an adhesive mixture (e.g., a mixture of Fastbond™ 30-NF Contact Adhesive and the surfactant Triton™ X-100 (Union Carbide, Danbury Conn.), 93%:7% wt/wt.) to a wet thickness of 25 μm onto 5 mil polyester film such as that sold under the trademark Melinex® "S" (duPont Polyester Films, Wilmington Del.) using a wire bar coater from Thomas Scientific, Swedesboro, N.J. The coated top foil was dried for 2 minutes at 50° C. in a horizontal air flow oven (VWR Scientific Products). The capillary chamber was opened by cutting 1 millimeter in from the front edge of the capillary chamber with a pair of scissors. The dried coated top foil was applied to the sensor, allowing approximately a 0.5 mm space between the back edge of the chamber and the edge of the top foil as an air vent. The top foil was sealed to the sensor surface using a 5 ton press with a heated top platen, at 81° C., 60 psi for 5 seconds. The panel of completed sensors was cut into individual sensors and stored desiccated at 8% RH until tested.

The sensors were evaluated using chronoamperometry electrochemical techniques on test stands such as that sold under the trademark of BAS® 100W Electrochemical Workstation, Bioanalytical Systems, Inc. West Lafayette, Ind. The preferred electrochemical test stand used in the evaluation of the electrodes was a dedicated test stand for DC chronoamperometric current measurement for assay potentials from ±1 volt.

The sensors may be used to determine the concentration of an analyte, such as glucose, in a fluid sample by performing the following steps:

Set up the test stand parameters:
  In accordance with a "drop detect" system, an initial potential difference is established between the working and counter electrodes—300 mV (millivolts)—to start timing of the analysis sequence. Current response to this potential is triggered by contact of the array with a fluid sample.
  The initial current response upon application of the test solution to the sensor chamber is generally greater than 0.4 microamps.
  The time (delay period) between the threshold trigger and re-application of the 300 mV potential difference (assay potential) is generally 3 seconds.
  The assay period, after re-application of the 300 mV potential difference between the working and counter electrodes of the sensor is generally 9 seconds.

In more detail:
  Insert the sensor into the test stand connection. Apply approximately 0.3 uL of a fluid sample to the opening of the capillary chamber. Fluid will flow into the chamber by capillary action covering the chemical coating applied to the working and counter electrodes. The threshold current will be triggered when the sample fluid covers the nearest working and counter electrode fingers. Once triggered, the potential difference will go to open circuit for a 3 seconds, during the delay period.
  During the delay period, reaction will occur between the reactants (analyte, enzyme/cofactor, and the oxidized form of the mediator), resulting in reduction of the mediator.
  The 300 mV assay potential difference is re-applied between the electrodes after the 3 second delay. This causes electro-oxidation of the reduced mediator at the surface of the working electrode.
  The current/time reaction profiles of the assay show a characteristic pseudo-steady-state current/time plateau starting 0.5 to 1.5 seconds after re-application of the 300 mV assay potential to the sensor. Currents at fixed assay period points chosen in this plateau region were proportional to the concentration of analyte in the sample fluid. Assay endpoints were chosen in such a manner give a linear dose response for glucose concentrations from 0 to 600 mg/dL. See FIG. 7.

The invention claimed is:

1. A method of determining the concentration of glucose in a blood sample, comprising:
   providing a disposable biosensor test strip including a capillary chamber having a depth suitable for capillary flow of blood and holding a volume of less than about 1.0 μl of the blood sample, a working electrode and a counter or reference electrode disposed within the capillary chamber, and a reagent proximal to or in contact with at least the working electrode, the reagent including an enzyme and a mediator, the reagent reacting with glucose to produce an electroactive reaction product;

applying a blood sample containing glucose into the capillary chamber, the capillary chamber directing capillary flow of the blood sample into contact with the reagent to cause the blood sample to at least partially solubilize or hydrate the reagent;

detecting the blood sample in the capillary chamber;

electrooxidizing or electroreducing the electroactive reaction product at the working electrode; and within 10 seconds after said detecting, determining and providing a readout of the glucose concentration in the blood sample, said determining comprising correlating the electrooxidized or electroreduced electroactive reaction product to the concentration of glucose in the blood sample.

2. The method of claim 1 in which said detecting comprises applying a dose-detect potential between the working and counter or reference electrodes, and recognizing a rise in current as an indication that the sample has been supplied to the capillary chamber.

3. The method of claim 1 in which the test strip includes a vent communicating with the capillary chamber to facilitate flow of the sample into the capillary chamber.

4. The method of claim 1 in which said providing comprises providing the reagent in a sufficiently small amount as to be solubilized or hydrated in a time sufficient to allow said determining and providing a readout of the glucose concentration in the sample within 10 seconds after said detecting.

5. The method of claim 1 in which said providing comprises providing a test strip including a bottom substrate, a spacing layer, and a top substrate, the spacing layer having an opening corresponding to the capillary chamber, the spacing layer substantially defining the depth of the capillary chamber.

6. The method of claim 5 in which the test strip is elongated with two opposed sides, the spacing layer comprising spaced-apart first and second portions defining a capillary chamber extending between and opening at the two opposed sides.

7. The method of claim 1 in which said providing comprises providing a mediator in its oxidized form.

8. The method of claim 7 in which the mediator reacts sufficiently rapidly as to allow said determining and providing a readout of the glucose concentration in the sample within 10 seconds after said detecting.

9. The method of claim 8 in which said providing comprises providing the reagent in a sufficiently small amount as to be solubilized or hydrated in a time sufficient to allow said determining and providing a readout of the glucose concentration in the sample within 10 seconds after said detecting.

10. The method of claim 9 in which the capillary chamber holds a volume of less than about 0.4 µl.

11. The method of claim 10 in which the capillary chamber holds a volume of between about 0.25 µl and about 0.4 µl.

12. The method of claim 11 in which said detecting comprises applying a dose-detect potential between the working and counter or reference electrodes, and recognizing a rise in current as an indication that the sample has been supplied to the capillary chamber.

13. The method of claim 12 in which the test strip includes a vent communicating with the capillary chamber to facilitate flow of the sample into the capillary chamber.

14. The method of claim 13 in which said providing comprises providing a test strip including a bottom substrate, a spacing layer, and a top substrate, the spacing layer having an opening corresponding to the capillary chamber, the spacing layer substantially defining the depth of the capillary chamber.

15. The method of claim 14 in which the test strip is elongated with two opposed sides, the spacing layer comprising spaced-apart first and second portions defining a capillary chamber extending between and opening at the two opposed sides.

16. The method of claim 1 in which the capillary chamber holds a volume of less than about 0.4 µl.

17. The method of claim 16 in which the capillary chamber holds a volume of between about 0.25 µl and about 0.4 µl.

18. The method of claim 1 in which said electroactive reaction product is capable of being electrooxidized or electroreduced at the working electrode, said determining comprising measuring the amount of electroactive reaction product electrooxidized or electroreduced, and correlating the amount of electrooxidized or electroreduced electroactive reaction product to the concentration of glucose in the blood sample.

19. The method of claim 1 in which said capillary chamber has a depth of 25–200 µm.

20. The method of claim 1 including automatically operating the test strip and timing the reaction and analysis of the blood sample to detect the blood sample in the capillary chamber, to electrooxidize the electroactive reaction product, and to determine and provide a readout of the glucose concentration within 10 seconds of said detecting.

21. The method of claim 1 in which the test strip comprises a counter electrode, and in which the reagent is located proximal to or in contact with the working and counter electrodes.

22. The method of claim 1 in which the capillary chamber holds a volume of about 600 nL.

23. The method of claim 22 comprising determining and providing a readout of the glucose concentration within about 5 seconds after said detecting.

24. The method of claim 1 in which the capillary chamber holds a volume of between 0.25 µl and 0.4 µl.

25. The method of claim 24 comprising determining and providing a readout of the glucose concentration within about 5 seconds after said detecting.

26. The method of claim 24 in which the capillary chamber holds a volume of about 400 nL.

27. The method of claim 26 comprising determining and providing a readout of the glucose concentration within about 5 seconds after said detecting.

28. The method of claim 24 in which the capillary chamber holds a volume of about 300 nL.

29. The method of claim 28 comprising determining and providing a readout of the glucose concentration within about 5 seconds after said detecting.

30. The method of claim 1 comprising determining and providing a readout of the glucose concentration within about 8 seconds of said detecting.

31. The method of claim 30 comprising determining and providing a readout of the glucose concentration about 3.5 to about 8 seconds after said detecting.

32. The method of claim 31 comprising determining and providing a readout of the glucose concentration within about 5 seconds of said detecting.

33. The method of claim 32 comprising determining and providing a readout of the glucose concentration within about 4 seconds of said detecting.

34. The method of claim 31 comprising determining and providing a readout of the glucose concentration about 5 seconds after said detecting.

35. The method of claim 31 comprising determining and providing a readout of the glucose concentration about 4 seconds after said detecting.

36. A method of determining the concentration of glucose in a blood sample, comprising:
providing a disposable biosensor test strip including a capillary chamber having a depth suitable for capillary flow of blood and holding a volume of less than about 1.0 μl of the blood sample, a working electrode and a counter or reference electrode disposed within the capillary chamber, and a reagent proximal to or in contact with at least the working electrode, the reagent including an enzyme and a mediator, the reagent reacting with glucose to produce an electroactive reaction product;
applying a blood sample containing glucose into the capillary chamber, the capillary chamber directing capillary flow of the blood sample into contact with the reagent to cause the blood sample to at least partially solubilize or hydrate the reagent;
detecting the blood sample in the capillary chamber;
electrooxidizing the electroactive reaction product at the working electrode; and
within 10 seconds after said detecting, determining and providing a readout of the glucose concentration in the blood sample, said determining comprising correlating the electrooxidized electroactive reaction product to the concentration of glucose in the blood sample.

37. The method of claim 36 in which the capillary chamber holds a volume of about 600 nL.

38. The method of claim 37 comprising determining and providing a readout of the glucose concentration within about 5 seconds after said detecting.

39. The method of claim 36 in which the capillary chamber holds a volume of between 0.25 μl and 0.4 μl.

40. The method of claim 39 comprising determining and providing a readout of the glucose concentration within about 5 seconds after said detecting.

41. The method of claim 39 in which the capillary chamber holds a volume of about 400 nL.

42. The method of claim 41 comprising determining and providing a readout of the glucose concentration within about 5 seconds after said detecting.

43. The method of claim 39 in which the capillary chamber holds a volume of about 300 nL.

44. The method of claim 43 comprising determining and providing a readout of the glucose concentration within about 5 seconds after said detecting.

45. The method of claim 36 comprising determining and providing a readout of the glucose concentration within about 8 seconds of said detecting.

46. The method of claim 45 comprising determining and providing a readout of the glucose concentration about 3.5 to about 8 seconds after said detecting.

47. The method of claim 46 comprising determining and providing a readout of the glucose concentration within about 5 seconds of said detecting.

48. The method of claim 47 comprising determining and providing a readout of the glucose concentration within about 4 seconds of said detecting.

49. The method of claim 46 comprising determining and providing a readout of the glucose concentration about 5 seconds after said detecting.

50. The method of claim 46 comprising determining and providing a readout of the glucose concentration about 4 seconds after said detecting.

51. The method of claim 36 in which the reagent is dry, and the capillary chamber directs capillary flow of the blood sample into contact with the dry reagent to cause the blood sample to at least partially solubilize or hydrate the dry reagent.

52. The method of claim 51 in which the dry reagent comprises a reagent that is applied wet and dried of solvent.

53. The method of claim 36 in which the capillary chamber has a depth of 25-200 μm.

54. The method of claim 36 in which said providing comprises providing the reagent in a sufficiently small amount as to be solubilized or hydrated in a time sufficiently fast to allow said determining and providing a readout of the glucose concentration in the blood sample within 10 seconds of said detecting.

55. The method of claim 54 in which the mediator reacts sufficiently rapidly as to allow determining and providing a readout of the glucose concentration in the blood sample within 10 seconds of said detecting.

56. The method of claim 55 in which the mediator is readily-reversible.

57. The method of claim 36 including automatically operating the test strip and timing the reaction and analysis of the blood sample to detect the blood sample in the capillary chamber, to electrooxidize the electroactive reaction product, and to determine and provide a readout of the glucose concentration within 10 seconds of said detecting.

58. The method of claim 57 in which said automatically operating comprises connecting the test strip to an external testing apparatus prior to said detecting, the testing apparatus automatically detecting the blood sample in the capillary chamber, electrooxidizing the electroactive reaction product, determining the glucose concentration, and providing a readout of the glucose concentration within 10 seconds of said detecting.

59. The method of claim 36 in which the working electrode and the counter or reference electrode are coplanar.

60. The method of claim 36 comprising measuring the current and correlating the measured current to the glucose concentration.

61. The method of claim 36 in which said detecting comprises applying a drop-detect potential across the working and counter or reference electrodes.

62. The method of claim 61 in which said detecting comprises applying a drop-detect potential across the working and counter or reference electrodes prior to and separate from said determining.

63. The method of claim 62 in which said detecting comprises applying a drop-detect potential across the working and counter or reference electrodes and recognizing a rise in current as an indication that the blood sample has been applied into the capillary chamber.

64. The method of claim 62 which includes reapplying a potential across the working and counter or reference electrodes, after a delay period during which no potential is applied, to electrooxidize the electroactive reaction product at the working electrode.

65. The method of claim 36 in which said providing comprises providing a test strip including a bottom substrate, a spacing layer, and a top substrate, the spacing layer having an opening corresponding to the capillary chamber, the spacing layer substantially defining the depth of the capillary chamber.

66. The method of claim 36 in which said reacting produces a reduced form of the mediator.

67. The method of claim 36 comprising measuring the amount of the electrooxidized electroactive reaction product and correlating the amount to the concentration of glucose in the blood sample.

68. The method of claim 36 comprising applying a potential of 100-500 mV across the working electrode and the counter or reference electrodes.

69. The method of claim 36 in which the test strip comprises a counter electrode, and in which the reagent is located proximal to or in contact with the working and counter electrodes.

* * * * *

(12) EX PARTE REEXAMINATION CERTIFICATE (6677th)
United States Patent
Wilsey

(10) Number: US 7,276,147 C1
(45) Certificate Issued: Feb. 24, 2009

(54) METHOD FOR DETERMINING THE CONCENTRATION OF AN ANALYTE IN A LIQUID SAMPLE USING SMALL VOLUME SAMPLES AND FAST TEST TIMES

(75) Inventor: Christopher D. Wilsey, Carmel, IN (US)

(73) Assignee: Corange International Limited, Hamilton (BM)

Reexamination Request:
No. 90/010,080, Dec. 14, 2007

Reexamination Certificate for:
Patent No.: 7,276,147
Issued: Oct. 2, 2007
Appl. No.: 10/382,322
Filed: Mar. 5, 2003

( * ) Notice: This patent is subject to a terminal disclaimer.

Related U.S. Application Data

(63) Continuation of application No. 10/264,785, filed on Oct. 4, 2002, now abandoned
(60) Provisional application No. 60/332,411, filed on Nov. 16, 2001.

(51) Int. Cl.
*G01N 27/327* (2006.01)

(52) U.S. Cl. .................... 205/792; 205/777.5; 204/403.4
(58) Field of Classification Search .................... None
See application file for complete search history.

(56) References Cited

U.S. PATENT DOCUMENTS 6,153,069 A 11/2000 Pottgen et al.

FOREIGN PATENT DOCUMENTS

WO WO 00/20626 A1 4/2000

*Primary Examiner*—Gary L Kunz

(57) ABSTRACT

Analytes in a liquid sample are determined by methods utilizing sample volumes of less than about 1.5 μl and test times within ten seconds. The methods are preferably performed using small test strips including a sample receiving chamber filled with the sample by capillary action.

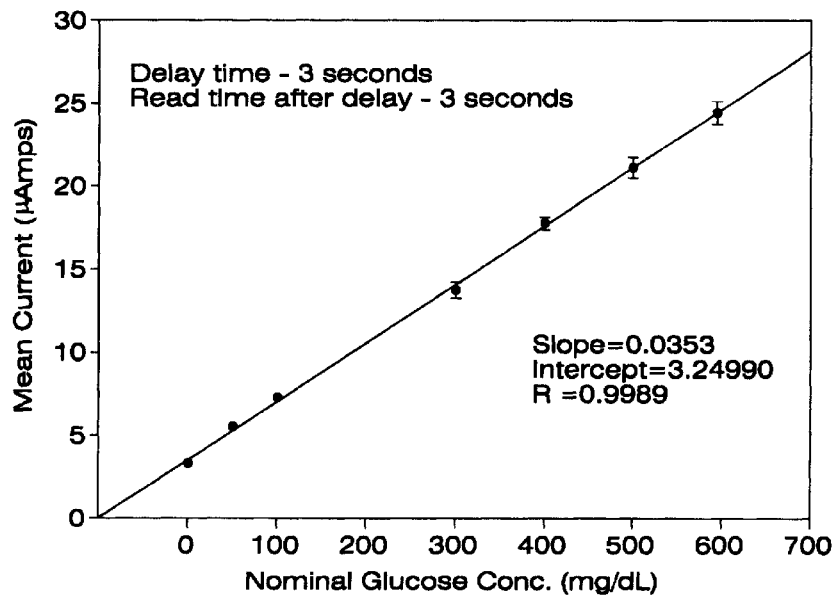

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 18, lines 20–32:

In fabricating the capillary, the depth of the chamber can be controlled by choosing the coverlay material or materials used, according to thickness. Vacrel 8140® [(] film has a thickness of 2, 3, or 4 mil (100 µm). Pyralux PC® 1000, 1500, have 2000 have maximum thicknesses of 2.5 mils (63.5 µm), so double layer lamination gives a chamber depth of 127 µm. Pyralux 1010 has a thickness of 1 mil or 25.4 µm. Capillaries with depths of greater than or equal to 100 µm have been found to allow fast fill of blood with hematocrits from 20 to 70% to reliably flow into the chamber. Capillary depths of less than 100 microns to 25 microns can be used for other biological fluids such as serum, plasma, intersticial fluid, and the like.

Figure 7:
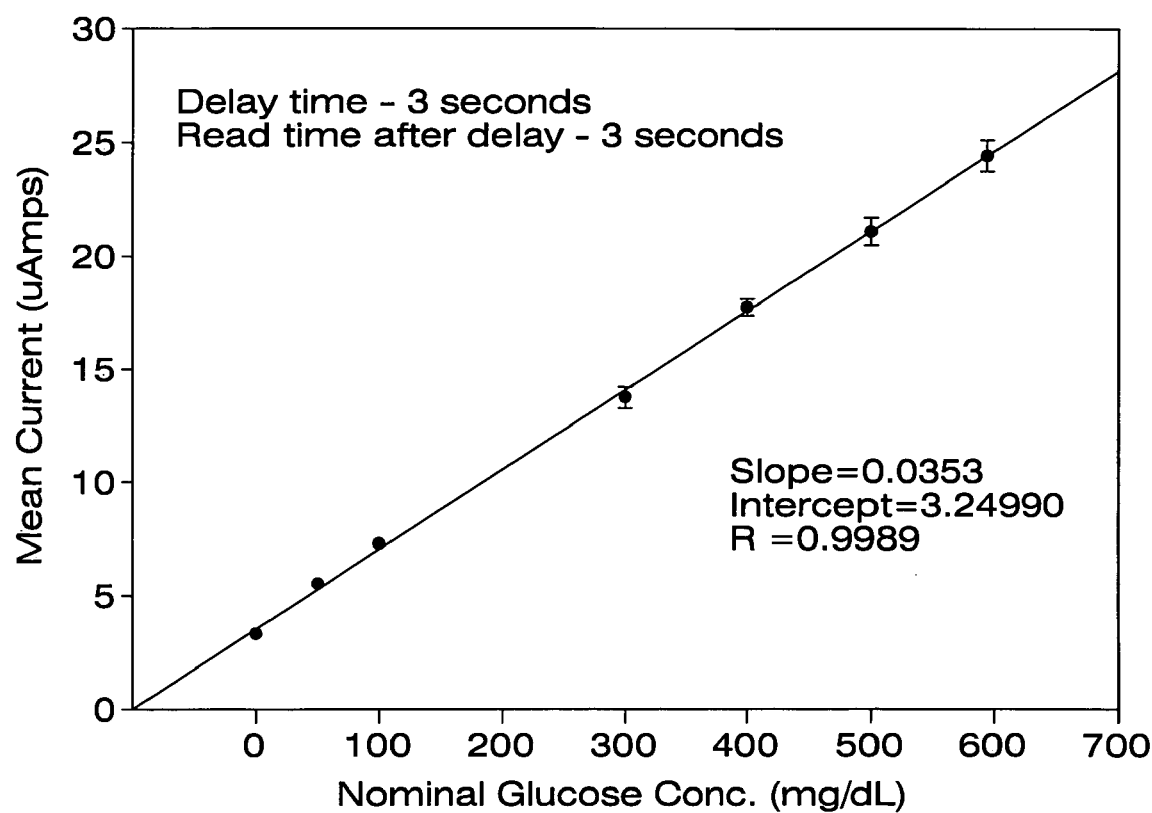
FIG. 7 shows data of assay current versus blood glucose level.
Figure 7:
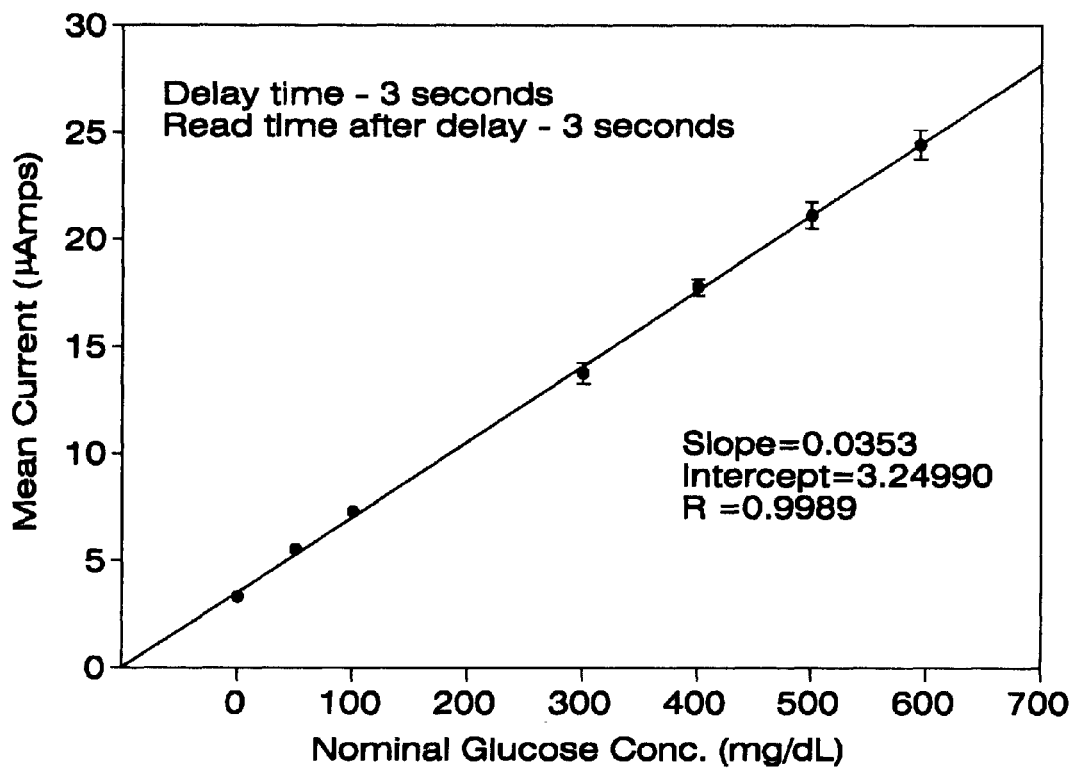

THE DRAWING FIGURES HAVE BEEN CHANGED AS FOLLOWS:

(uAmps) to (µAmps) in FIG. 7.

AS A RESULT OF REEXAMINATION, IT HAS BEEN DETERMINED THAT:

The patentability of claims 1–56 and 59–69 is confirmed.

Claim 57 is determined to be patentable as amended.

Claim 58, dependent on an amended claim, is determined to be patentable.

57. The method of claim 36 including automatically operating the test strip and timing the reaction and analysis of the blood sample to detect the blood sample in the capillary chamber, to electrooxidize the electroactive reaction product, and to [detennine] *determine* and provide a readout of the glucose concentration within 10 seconds of said detecting.

* * * * *